US012100511B1

(12) United States Patent
Aranke et al.

(10) Patent No.: US 12,100,511 B1
(45) Date of Patent: *Sep. 24, 2024

(54) HEALTH CARE MANAGEMENT USING A TOTAL HEALTH INDEX

(71) Applicant: Kaiser Foundation Hospitals, Oakland, CA (US)

(72) Inventors: Sarang Aranke, Irvine, CA (US); Suman K. Mishra, San Ramon, CA (US); Pratabkumar Vemana, Oakland, CA (US)

(73) Assignee: KAISER FOUNDATION HOSPITALS, Oakland, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/524,846

(22) Filed: Nov. 12, 2021

Related U.S. Application Data

(60) Provisional application No. 63/113,823, filed on Nov. 13, 2020.

(51) Int. Cl.
*G16H 50/20* (2018.01)
*G08B 21/24* (2006.01)
(Continued)

(52) U.S. Cl.
CPC ............. *G16H 50/20* (2018.01); *G08B 21/24* (2013.01); *G16H 10/60* (2018.01); *G16H 20/10* (2018.01);
(Continued)

(58) Field of Classification Search
None
See application file for complete search history.

(56) References Cited

U.S. PATENT DOCUMENTS 6,578,003 B1* 6/2003 Camarda ................ G16H 20/10
705/2
7,685,000 B1* 3/2010 Petit ....................... G16H 50/80
705/2
(Continued)

FOREIGN PATENT DOCUMENTS

GB 2482193 A 1/2012
WO 2020/191267 9/2020
WO WO-2020191267 A1 * 9/2020 ............ A61J 7/0076

OTHER PUBLICATIONS

Feng Xie et al., AutoScore: A Machine Learning-Based Automatic Clinical Score Generator and Its Application to Mortality Prediction Using Electronic Health Records, JMIR Med Inform 2020; 8(10):e21798, https://medinform.jmir.org/2020/10/e21798 (last visited Apr. 25, 2024), DOI: 10.2196/21798 (Year: 2020).*
(Continued)

*Primary Examiner* — Jonathon A. Szumny
*Assistant Examiner* — Nicholas Akogyeram, II
(74) *Attorney, Agent, or Firm* — PATENT LAW WORKS LLP

(57) ABSTRACT

A system and method for generating a total health index and recommending an actionable intervention for managing a health risk of a patient is disclosed. The method includes receiving user-generated data, clinical data, and pharmacy data in association with a patient, determining a social health index score based on the user-generated data, determining a clinical risk index score based on the clinical data, determining a medication adherence index score based on the pharmacy data, determining, using a machine learning model on one or more of the social health index score, the clinical risk index score, and the medication adherence index score, a total health index score and an actionable intervention for managing a health risk in association with the patient based on the total health index score, and automatically initiating the actionable intervention.

20 Claims, 11 Drawing Sheets

(51) Int. Cl.
- *G16H 10/60* (2018.01)
- *G16H 20/10* (2018.01)
- *G16H 40/20* (2018.01)
- *G16H 50/30* (2018.01)
- *G06Q 10/1093* (2023.01)
- *G06Q 50/22* (2018.01)
- *G16H 40/67* (2018.01)

(52) U.S. Cl.
CPC ............ *G16H 40/20* (2018.01); *G16H 50/30* (2018.01); *G06Q 10/1093* (2013.01); *G06Q 50/22* (2013.01); *G16H 40/67* (2018.01)

(56) References Cited

U.S. PATENT DOCUMENTS

| | | | | |
|---|---|---|---|---|
| 2003/0212579 | A1* | 11/2003 | Brown | A61B 5/411 600/300 |
| 2011/0215933 | A1* | 9/2011 | Darling, IV | G06Q 10/109 340/573.1 |
| 2012/0179480 | A1* | 7/2012 | Patel | G16H 10/20 705/2 |
| 2015/0294078 | A1* | 10/2015 | Geleijnse | G16H 10/60 705/3 |
| 2016/0232805 | A1* | 8/2016 | Gibson | G16H 20/10 |
| 2018/0075207 | A1* | 3/2018 | Schmidt | G16H 50/30 |
| 2019/0074090 | A1 | 3/2019 | Ronen | |
| 2019/0083031 | A1* | 3/2019 | Hanina | A61B 5/1128 |
| 2019/0088356 | A1* | 3/2019 | Oliver | G09B 23/28 |
| 2019/0310891 | A1* | 10/2019 | Baldasaro | G06F 9/542 |

OTHER PUBLICATIONS

Feng Xie et al., AutoScore: A Machine Learning-Based Automatic Clinical Score Generator and Its Application to Mortality Prediction Using Electronic Health Records, JMIR Med Inform 2020; 8(10):e21798, https://medinform.jmir.org/2020/10/e21798 (last visited Jul. 13, 2023), DOI: 10.2196/21798 (Year: 2020).

* cited by examiner

300c →

Medication
5 medications

Ready for refill

Medication name
Last filed on: N/A
Refills remaining: 2
Status: available for refill
RX no: 179100089066
⊕ View more medications
— 318

Test results
1 recent result

Most recent test
Hemoglobin A1C
4.1%
Taken on July 1, 2020
More info
⊕ View more test results
— 320

Support
Contact care team or wellness coach
— 322

300d →

Wellness apps

Lorem ipsum dolor sit amet, consectetur adipiscing elit. Aliquam urna tellus, tempus quis neque quis, pulvinar sollicitudin arcu.

Calm
Calm is the #1 app for meditation and sleep – designed to help lower stress, reduce anxiety, and more.

myStrength
myStrength is a personalized program that helps improve your awareness and change behaviors. Explore interactive, in-the-moment coping tools, community support, and more.

ClassPass
ClassPass makes it easier for you to work out from anywhere. ClassPass partners with gyms and studios that offer a range of classes including yoga, dance, cardio, boxing, pilates, and more.

⊕ Find Care
— 324

Figure 3B

| Region ▽ | Area ▽ | Medical Office Building ▽ | Individual ▽ | | | | | | | | | Export |
|---|---|---|---|---|---|---|---|---|---|---|---|---|

Filter Settings: Age ▽ | Full Name ▽ | Gender ▽ | Primary Language ▽ | LEP Status ▽
MOB ▽ | Rx ID ▽ | Rx Name ▽ | Predicted PDC Score ▽

Average PDC Score 0.74 | Number of records: 328 | Number of patients: 300 | 30% LEP in Los Angeles

| MRN | Full Name | Phone # | Action | Primary Language | Med ID | Predicted PDC | Age | MOB | Order Type | Rx ID | Rx Name | Rx Refill Date | Outreach Date |
|---|---|---|---|---|---|---|---|---|---|---|---|---|---|
| ### | Sue A. Smith | (123) 456-7890 | SMS-Remind | English | Ex 1 | 0.90 | 35 | Riverside MOB | Picked up at pharmacy | #### | Ibuprofen | 08/20/2020 | 08/20/2020 |
| ### | Ravi | (###) ###-#### | SMS-Educate | English | Ex 4 | 0.88 | 55 | Riverside MOB | Mailed | #### | Ibuprofen | 08/30/2020 | 08/28/2020 |
| ### | Joe | (###) ###-#### | SMS-Educate | Spanish | Ex 2 | 0.72 | 48 | Barranca MOB | Mailed | #### | Melatonin | 08/23/2020 | 08/25/2020 |
| ### | Kat | (###) ###-#### | SMS-Remind | Spanish | Ex 5 | 0.61 | 68 | Sand Canyon MOB | Picked up at pharmacy | #### | Ibuprofen | 09/04/2020 | 08/30/2020 |
| ### | Jon | (###) ###-#### | SMS-Educate | English | Ex 3 | 0.34 | 50 | Barranca MOB | Picked up at pharmacy | #### | Melatonin | 09/15/2020 | 08/28/2020 |

Figure 5

HEALTH CARE MANAGEMENT USING A TOTAL HEALTH INDEX

CROSS-REFERENCE TO RELATED APPLICATIONS

The present application claims priority, under 35 U.S.C. § 119, of U.S. Provisional Patent Application No. 63/113,823, filed Nov. 13, 2020, and entitled "Total Health Index System and Method," which is incorporated by reference in its entirety.

BACKGROUND

This specification generally relates to managing health care outcomes and medication adherence in patients with chronic conditions. In particular, the specification relates to a system and method for generating a total health index and recommending an actionable intervention for managing a health risk of a patient using one or more trained machine learning models.

Oftentimes, patients of a health care provider struggle with managing their health conditions. Facing a new diagnosis is overwhelming to such patients and the engagement levels with managing their health conditions change over time. It is critical for the patients to understand and manage their health conditions while adhering to taking their prescribed medications. However, health care providers are limited in their capability to facilitate and guide their patients with this lifestyle management. There is a persistent need to personalize the patient experience in the massive and yet slow-moving health care industry and automate intelligent, timely, and targeted patient interventions to support patients with taking appropriate actions to stay in control of their health conditions and reduce health care costs.

Furthermore, health care providers and hospitals categorize patient conditions to track and evaluate patients. However, while health care providers are tracking these patient conditions, they are only tracking single conditions, such as a specific injury, specific laboratory results, etc., that are related to that patient. Health care providers and hospitals are unable to track more than those single conditions that are being tracked and evaluated. Since health care providers and hospitals are limited to only tracking the single conditions, they are unable to measure the total health condition of a patient.

This background description provided herein is for the purpose of generally presenting the context of the disclosure.

SUMMARY

The techniques introduced herein overcome the deficiencies and limitations of the prior art at least in part by providing systems and methods for generating a total health index and recommending an actionable intervention for managing a health risk of a patient.

According to one innovative aspect of the subject matter described in this disclosure, a method includes: receiving user-generated data, clinical data, and pharmacy data in association with a patient; determining a social health index score based on the user-generated data; determining a clinical risk index score based on the clinical data; determining a medication adherence index score based on the pharmacy data; determining, using a machine learning model and one or more of the social health index score, the clinical risk index score, and the medication adherence index score, a total health index score and an actionable intervention for managing a health risk in association with the patient based on the total health index score; and automatically initiating the actionable intervention.

According to another innovative aspect of the subject matter described in this disclosure, a system includes: one or more processors; a memory storing instructions, which when executed cause the one or more processors to: receive user-generated data, clinical data, and pharmacy data in association with a patient; determine a social health index score based on the user-generated data; determine a clinical risk index score based on the clinical data;

determining a medication adherence index score based on the pharmacy data; determine, using a machine learning model on one or more of the social health index score, the clinical risk index score, and the medication adherence index score, a total health index score and an actionable intervention for managing a health risk in association with the patient based on the total health index score; and automatically initiate the actionable intervention.

These and other implementations may each optionally include one or more of the following operations. For instance, the operations may include: generating a dashboard for condition management, the dashboard providing access to one or more of protected health information indicators and status, educational content recommendations, medication planning and reminders, appointment management, and social and emotional support groups; presenting the dashboard for condition management to the patient; determining a population of patients to target for a medication adherence campaign; dividing the population of patients into a test group and a control group; identifying a plurality of patients in the test group at risk of non-adherence to medication; determining one or more actionable interventions for at-risk patients from the plurality of patients in the test group; aggregating data resulting from the one or more actionable interventions; and generating one or more dashboards for the medication adherence campaign based on the aggregated data. Additionally, these and other implementations may each optionally include one or more of the following features. For instance, the features may include: determining the actionable intervention for managing the health risk comprising determining, from an output of the machine learning model, that the health risk is a likelihood of the patient missing an upcoming healthcare appointment scheduled with a healthcare provider, identifying a communication channel preferred by the patient, and determining the actionable intervention to send an additional notification reminding the patient about the upcoming healthcare appointment through the identified communication channel; determining, from an output of the machine learning model, that the health risk is a likelihood of a health condition progressing in the patient, and determining the actionable intervention to recommend content to the patient, the content associated with educating the patient about reducing a progression of the health condition; determining, from an output of the machine learning model, that the health risk is a likelihood of a comorbidity in the patient, and determining the actionable intervention to schedule an appointment with a healthcare provider of the patient for medically testing a disease associated with the comorbidity in the patient; determining, from an output of the machine learning model, that the health risk is a likelihood of a medication adherence score of the patient being less than a threshold by end of a predetermined time period, and determining the actionable intervention from a group of a digital intervention, an educational intervention, and a social intervention to facilitate the patient with adhering to taking their prescribed medication; the digital intervention including sending a reminder notification through one or more of a phone call, text messaging, email, in-app messaging within a health care mobile application, and an interactive voice response; the educational intervention including sending a comic strip including a story about a benefit associated with adhering to taking prescribed medication; and the social intervention including one or more of scheduling an appointment with a social work for a counseling session, informing a family member of the patient to help with medication adherence, and sending a reminder in a native language of the patient with limited English proficiency.

Other implementations of one or more of these aspects and other aspects include corresponding systems, apparatus, and computer programs, configured to perform the various action and/or store various data described in association with these aspects. Numerous additional features may be included in these and various other implementations, as discussed throughout this disclosure.

The features and advantages described herein are not all-inclusive and many additional features and advantages will be apparent in view of the figures and description. Moreover, it should be understood that the language used in the present disclosure has been principally selected for readability and instructional purposes, and not to limit the scope of the subject matter disclosed herein.

BRIEF DESCRIPTION OF THE DRAWINGS

The disclosure is illustrated by way of example, and not by way of limitation in the figures of the accompanying drawings in which like reference numerals are used to refer to similar elements.

FIGS. 3A-3B show graphical representations illustrating example user interfaces for presenting a dashboard for condition management to a user according to some implementations.

FIG. 5 shows a graphical representation of an example user interface for a dashboard identifying patient members to contact with an actionable intervention according to some implementations.

DETAILED DESCRIPTION

The present disclosure relates to generating a total health index for a user or patient. The total health index can be used to make determinations and direct interventions for a user. In one implementation, the total health index can be used for condition management, where data about the user is collected for the total health index and based on that total health index, actions are determined in order to manage the condition and/or care of the user. In another implementation, the total health index can be used for medication adherence, where data about the user is collected for the total health index and based on the total health index, actions are determined in order to increase the user's engagement with their medication protocols.

The total health index may be based on one or more indexes, such as a social health index of the user, a clinical risk index of the user, or a medication adherence index of the user. Each of these different indexes may be generated based on data collected from various data channels and may incorporate machine learning or other artificial intelligence in order to make determinations for each of the index scores as described elsewhere herein. These index scores may then be used to generate the total health index score. In some implementations, the total health index score may be generated by giving different weight factors to each of the indexes. These weight factors may be determined by machine learning or other artificial intelligence and may be updated over time as the models change based on the data collected.

Figure 1:
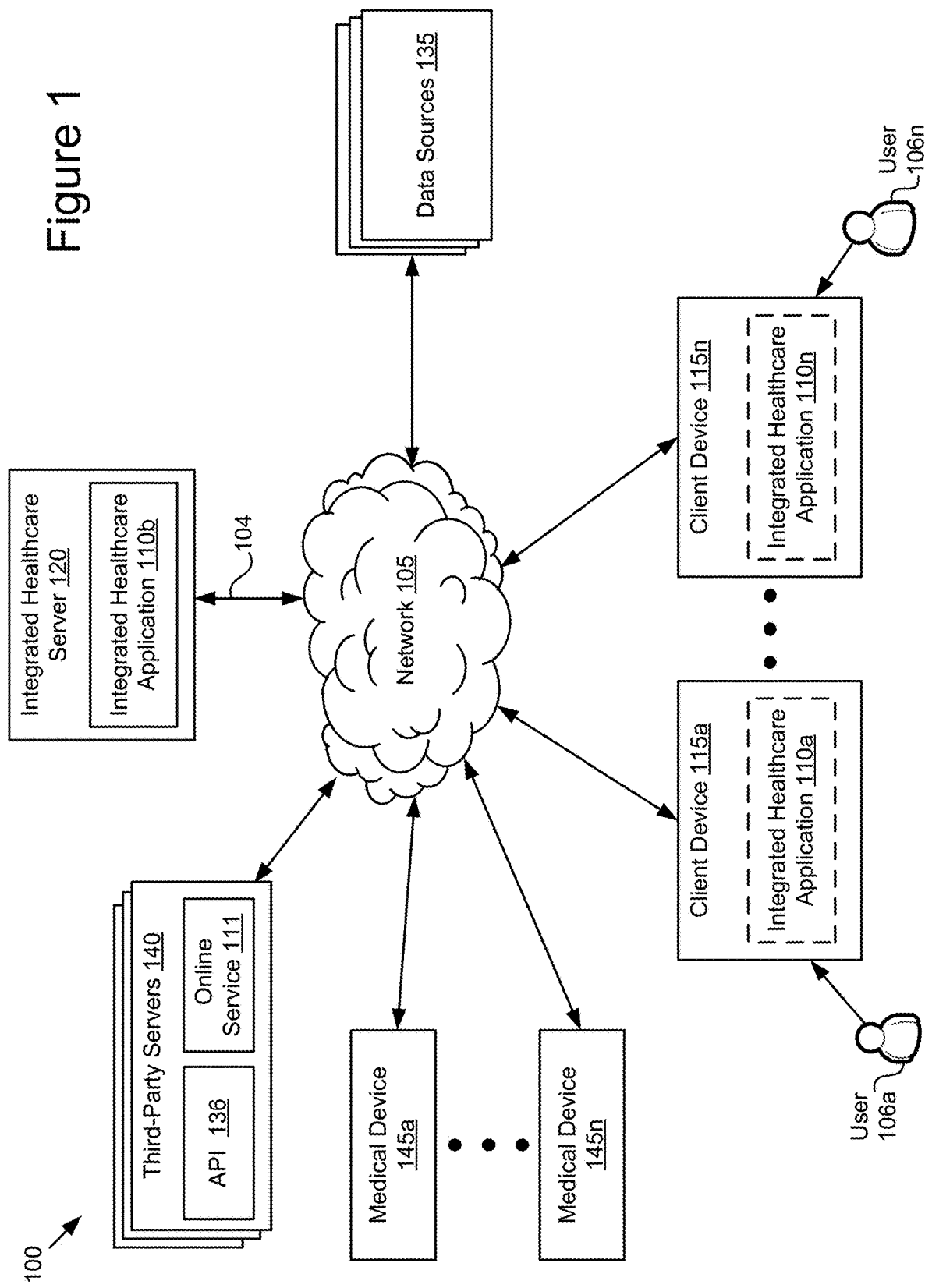
FIG. 1 is a high-level block diagram illustrating one implementation of an example system for generating a total health index and recommending an actionable intervention for managing a health risk of a patient.

FIG. 1 is a high-level block diagram illustrating one implementation of an example system 100 for generating a total health index and recommending an actionable intervention for managing a health risk of a patient. The illustrated system 100 may include one or more client devices 115a . . . 115n that can be accessed by users, an integrated healthcare server 120, a plurality of data sources 135, a plurality of third-party servers 140, and one or more medical devices 145a . . . 145n which are communicatively coupled via a network 105 for interaction and electronic communication with one another. In FIG. 1 and the remaining figures, a letter after a reference number, e.g., "115a," represents a reference to the element having that particular reference number. A reference number in the text without a following letter, e.g., "115," represents a general reference to instances of the element bearing that reference number The network 105 may be a conventional type, wired or wireless, and may have numerous different configurations including a star configuration, token ring configuration, or other configurations. Furthermore, the network 105 may include any number of networks and/or network types. For example, the network 105 may include a local area network (LAN), a wide area network (WAN) (e.g., the Internet), virtual private networks (VPNs), mobile (cellular) networks, wireless wide area network (WWANs), WiMAX® networks, Bluetooth® communication networks, peer-to-peer networks, near field networks (e.g., NFC, etc.), and/or other interconnected data paths across which multiple devices may communicate, various combinations thereof, etc. The network 105 may also be coupled to or include portions of a telecommunications network for sending data in a variety of different communication protocols. In some implementations, the network 105 may include Bluetooth communication networks or a cellular communications network for sending and receiving data including via short messaging service (SMS), multimedia messaging service (MMS), hypertext transfer protocol (HTTP), direct data connection, WAP, email, etc. In some implementations, the data transmitted by the network 105 may include packetized data (e.g., Internet Protocol (IP) data packets) that is routed to designated computing devices coupled to the network 105. Although FIG. 1 illustrates one network 105 coupled to the client devices 115, the integrated healthcare server 120, the plurality of data sources 135, the plurality of third-party servers 140, and the medical devices 145, in practice one or more networks 105 can be connected to these entities.

The client devices 115a . . . 115n (also referred to individually and collectively as 115) may be computing devices having data processing and communication capabilities. In some implementations, a client device 115 may include a memory, a processor (e.g., virtual, physical, etc.), a power source, a network interface, software and/or hardware components, such as a display, graphics processing unit (GPU), wireless transceivers, keyboard, camera (e.g., webcam), sensors, firmware, operating systems, web browsers, applications, drivers, and various physical connection interfaces (e.g., USB, HDMI, etc.). The client devices 115a . . . 115n may couple to and communicate with one another and the other entities of the system 100 via the network 105 using a wireless and/or wired connection. Examples of client devices 115 may include, but are not limited to, laptops, desktops, tablets, mobile phones (e.g., smartphones, feature phones, etc.), server appliances, servers, virtual machines, smart TVs, media streaming devices, user wearable computing devices (e.g., fitness trackers, etc.) or any other electronic device capable of accessing a network 105. In the example of FIG. 1, the client device 115a is configured to implement an integrated healthcare application 110a described in more detail below. The client device 115 includes a display for viewing information provided by one or more entities coupled to the network 105. For example, the client device 115 may be adapted to send and receive data to and from the integrated healthcare server 120. While two or more client devices 115 are depicted in FIG. 1, the system 100 may include any number of client devices 115. In addition, the client devices 115a . . . 115n may be the same or different types of computing devices. The client devices 115a . . . 115n may be associated with the users 106a . . . 106n. For example, users 106a . . . 106n may include patient members, physicians, clinical staff, lab technicians, administrative staff, etc. of a health care organization. Each client device 115 may be associated with a data channel, such as a mobile application running on a user's smartphone, a computer in a doctor's office, a health tracking device, etc. These data channels may collect data related to one or more users and provide that data to the entities coupled to the network 105. In some implementations, the client devices 115 may be implemented as a computing device 200 as will be described below with reference to FIG. 2.

The medical devices 145a . . . 145n may include, but are not limited to, a stethoscope, a blood pressure meter, a pulse oximeter, a thermometer, an ophthalmoscope, a weight and height scale, an otoscope, a camera, a telecardiology device (e.g. an ECG machine), a telepathology device (e.g. a microscope), a teledermatology device (e.g. a high-resolution camera), a teleradiology device (e.g. an ultrasound machine), a medical radiography equipment (e.g., MRI machine, CT machine, X-ray machine, etc.), etc. associated with one or more health care organizations. Authorized personnel who are trained to use the medical device 145 may obtain the patient's medical information. For example, the authorized personnel may include physicians and clinical staff. In some implementations, the medical device 145 may cooperate with the client device 115 to allow authorized personnel to communicate with other entities of the system 100. For example, the client device 115 receives a report associated with a patient including a medical test result from the medical device 145, and sends the report to the integrated healthcare server 120 for storage and analysis.

In the example of FIG. 1, each one of the integrated healthcare server 120, the plurality of data sources 135, and the plurality of the third-party servers 140 may be, or may be implemented by, a computing device including a processor, a memory, applications, a database, and network communication capabilities similar to that described below with reference to FIG. 2.

In the example of FIG. 1, the integrated healthcare server 120 may be configured to implement an integrated healthcare application 110b. In some implementations, the integrated healthcare server 120 may be a hardware server, a software server, or a combination of software and hardware. For example, the integrated healthcare server 120 may include one or more hardware servers, virtual servers, server arrays, storage devices and/or systems, etc., and/or may be centralized or distributed/cloud-based. In some implementations, the integrated healthcare server 120 may include one or more virtual servers, which operate in a host server environment and access the physical hardware of the host server including, for example, a processor, a memory, applications, a database, storage, network interfaces, etc., via an abstraction layer (e.g., a virtual machine manager). In some implementations, the integrated healthcare server 120 may be a Hypertext Transfer Protocol (HTTP) server, a Representational State Transfer (REST) service, or other server type, having structure and/or functionality for processing and satisfying content requests and/or receiving content from one or more of the client devices 115, one or more of the medical devices 145, the plurality of data sources 135, and the plurality of third-party servers 140 that are coupled to the network 105.

Also, instead of or in addition, the integrated healthcare server 120 may implement its own application programming interface (API) for the transmission of instructions, data, results, and other information between the server 120 and other entities communicatively coupled to the network 105. For example, the API may be a software interface exposed over the HTTP protocol by the integrated healthcare server 120. The API exposes internal data and functionality of the service hosted by the integrated healthcare server 101 to API requests originating from one or more of the integrated healthcare application 110, the plurality of data sources server 135, and the plurality of third-party servers 140. In one example, the integrated healthcare application 110b implemented by the integrated healthcare server 120 passes an authenticated request including a set of parameters for information to one or more of the third-party server 140 and the data source 135 and receives an object (e.g., XML or JSON) with associated results. In some implementations, the integrated healthcare server 120 may also include a database coupled to it (e.g., over the network 105) to store structured data in a relational database and a file system (e.g., HDFS, NFS, etc.) for unstructured or semi-structured data. In some implementations, the integrated healthcare server 120 may include an instance of a data store that stores various types of data for access and/or retrieval by the integrated healthcare application 110. For example, the data store may store user data associated with various users. The user data may include a user identifier (ID) uniquely identifying the users, a user profile, one or more data metrics of the users corresponding to data received from one or more channels. Other types of user data are also possible and contemplated.

In some implementations, the integrated healthcare server 120 sends and receives data to and from other entities of the system 100 via the network 105. For example, the integrated healthcare server 120 sends and receives data including instructions to and from the client device 115. In some implementations, the integrated healthcare server 120 may serve as a middle layer and permit interactions between the client device 115 and the plurality of the third-party servers 140 and the data sources 135 to flow through and from the integrated healthcare server 120 for security and convenience. In some implementations, the integrated healthcare server 120 may be operable to receive, store, and/or integrate variety of diverse user data, generate a total health index, determine actionable interventions using one or more trained machine learning models, automatically execute the actionable interventions to manage a health risk of patients, etc. The integrated healthcare server 120 may send data to and receive data from the other entities of the system 100 via the network 105. It should be understood that the integrated healthcare server 120 is not limited to providing the above-noted acts and/or functionality and may include other network-accessible services. In addition, while a single integrated healthcare server 120 is depicted in FIG. 1A, it should be understood that there may be any number of integrated healthcare servers 120 or a server cluster.

Each of the one or more third-party servers 140 may be, or may be implemented by, a computing device including a processor, a memory, applications, a database, and network communication capabilities. A third-party server 140 may be a Hypertext Transfer Protocol (HTTP) server, a Representational State Transfer (REST) service, or other server type, having structure and/or functionality for processing and satisfying content requests and/or receiving content from one or more of the client devices 115, the medical devices 145, and the integrated healthcare server 120 that are coupled to the network 105. In some implementations, the third-party server 140 may include an online service 111 dedicated to providing access to various services and information resources hosted by the third-party server 140 via web, mobile, and/or cloud applications. The online service 111 may obtain and store user data, user-generated data, content items (e.g., videos, text, images, etc.), and interaction data reflecting the interaction of users with the content items. In some implementations, the third-party server 140 may provide an API 136 to access the third-party server 140. User-generated data, as described herein, may include one or more of user profile information (e.g., user id, user preferences, user history, social network connections, etc.), logged information (e.g., heart rate, activity metrics, sleep quality data, calories and nutrient data, user device specific information, historical actions, etc.), and other user specific information. In some implementations, the online service 111 allows users to share content with other users (e.g., friends, contacts, public, similar users, etc.), purchase and/or view items (e.g., e-books, videos, music, games, subscription, fitness products, exercise equipment, etc.), and other similar actions. For example, the online service 111 may provide various services such as digital fitness content; personal training; running and cycling tracking service; music streaming service; mobile health (mHealth) service; video streaming service; web mapping service; multimedia messaging service; electronic mail service; news service; news aggregator service; social networking service; location-based service; photo and video-sharing social networking service; sleep-tracking service; diet-tracking and calorie counting service; ridesharing service; online banking service; online information database service; travel service; online e-commerce marketplace; ratings and review service; restaurant-reservation service; food delivery service; search service; health and fitness service; home automation and security service; Internet of Things (IOT), multimedia hosting, distribution, and sharing service; cloud-based data storage and sharing service; a combination of one or more of the foregoing services; or any other service where users retrieve, collaborate, and/or share information, etc. It should be noted that the list of items provided above as examples for the online service 111 above are not exhaustive and that others are contemplated in the techniques described herein.

Each of the plurality of data sources 135 may be, or may be implemented by, a computing device including a processor, a memory, applications, a database, and network communication capabilities. In some implementations, the data sources may be a data warehouse, a system of record (SOR), or belonging to a data repository owned by an organization that provides real-time or close to real-time data automatically or responsive to being polled or queried by the integrated healthcare server 120. Each of the plurality of data sources 135 may be associated with a first or third-party entity (e.g., a server associated with a separate company or service provider), such as a health insurance organization, a health care organization, world health organization, an independent health care provider, a healthcare software company, an Electronic Medical Record (EMR) software company, an Electronic Health Record (EHR) software company, a pharmacy management system, a drug research institute, a patient management software system, a clinical decision support system, a patient-satisfaction measurement firm, a medication adherence tracking system, a public-records database, a data mining platform, a Software as a Service (SaaS) data analytics company, a data science and machine learning platform, news site, support groups, health blogs, etc. Examples of data provided by the plurality of data sources 135 may include, but is not limited to, pharmacy data, physician-patient encounter data, clinical data, patient data, EMR, EHR, patient diagnosis data, patient procedures, appointment notes, socioeconomic data, social determinant data, demographic data, health plan data, prescription data, medication data, pharmaceutical data, survey data, medication adherence data, machine learning models, machine learning-based data analysis results, etc. In some implementations, each of the plurality of data sources 135 may be configured to provide or facilitate an API that allows the integrated healthcare application 110 to access data and information for performing the functionality described herein.

The integrated healthcare application 110 may include software and/or logic to provide the functionality for generating a total health index and recommending an actionable intervention for managing a health risk of a patient. In some implementations, the integrated healthcare application 110 may be implemented using programmable or specialized hardware, such as a field-programmable gate array (FPGA) or an application-specific integrated circuit (ASIC). In some implementations, the integrated healthcare application 110 may be implemented using a combination of hardware and software. In one implementation, the integrated healthcare application 110b is stored and executed on integrated healthcare server 120 alone. In another implementation, the integrated healthcare application 110a, 110n is stored and executed on client device 115 alone. In other implementations, the integrated healthcare application 110 may be stored and executed on various combinations of the medical devices 145, the client device 115, the data sources, the third-party servers, and the integrated healthcare server 120, or by any one of the medical devices 145, the client device 115 or the integrated healthcare server 120.

In some implementations, the integrated healthcare application 110a may be a thin-client application with some functionality executed on the client device 115 and additional functionality executed on the integrated healthcare server 120 by the integrated healthcare application 110b. In some implementations, the integrated healthcare application 110 may generate and present various user interfaces to perform these acts and/or functionality, which may in some cases be based at least in part on information received from the integrated healthcare server 120, the client device 115, the medical device 145, one or more of the third-party servers 140 and/or the data sources 135 via the network 105. Non-limiting example user interfaces that may be generated for display by the integrated healthcare application 110 are depicted in FIGS. 3A-3B, 4A-4B, 5, and 6. In some implementations, the integrated healthcare application 110 is code operable in a web browser, a web application accessible via a web browser, a native application (e.g., mobile application, installed application, etc.) on the client device 115, a combination thereof, etc. Additional structure, acts, and/or functionality of the integrated healthcare application 110 is further discussed below with reference to at least FIG. 2A.

In some implementations, the integrated healthcare application 110 may require users to be registered with the integrated healthcare server 120 to access the acts and/or functionality described herein. For example, to access various acts and/or functionality provided by the integrated healthcare application 110, the integrated healthcare application 110 may require a user to authenticate his/her identity. For example, the integrated healthcare application 110 may require a user seeking access to authenticate their identity by inputting credentials in an associated user interface. In another example, the integrated healthcare application 110 may interact with a federated identity server (not shown) to register and/or authenticate the user by scanning and verifying biometrics including facial attributes, fingerprint, and voice.

Other variations and/or combinations are also possible and contemplated. It should be understood that the system 100 illustrated in FIG. 1 is representative of an example system and that a variety of different system environments and configurations are contemplated and are within the scope of the present disclosure. For example, various acts and/or functionality may be moved from a server 120 to a client device 115, or vice versa, data may be consolidated into a single data store or further segmented into additional data stores, and some implementations may include additional or fewer computing devices, services, and/or networks, and may implement various functionality client or server-side. Furthermore, various entities of the system may be integrated into a single computing device or system or divided into additional computing devices or systems, etc.

Figure 2A:
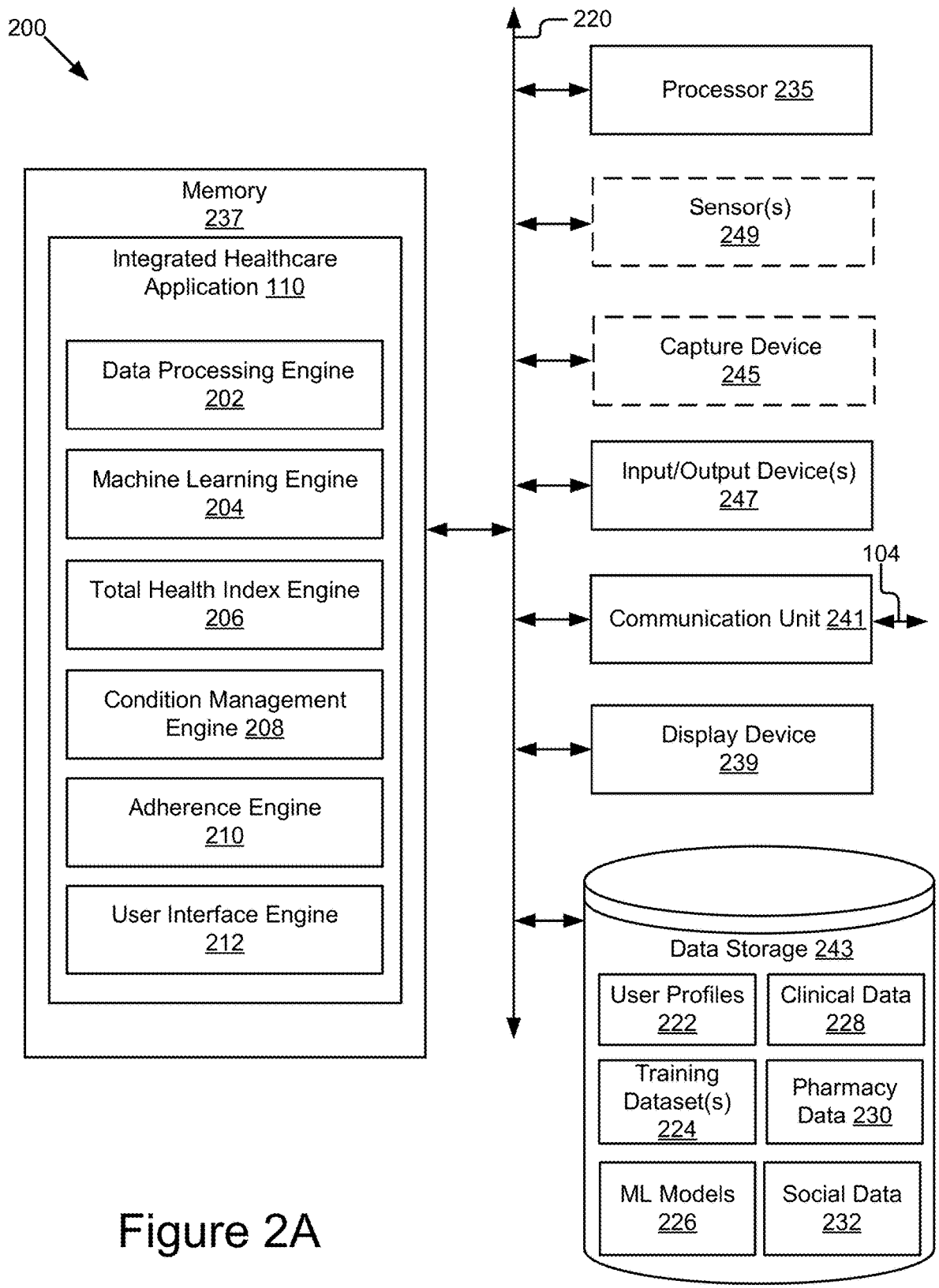
FIG. 2A is a block diagram illustrating one implementation of a computing device including an integrated healthcare application.

FIG. 2A is a block diagram illustrating one implementation of a computing device 200 including an integrated healthcare application 110. The computing device 200 may also include a processor 235, a memory 237, a display device 239, a communication unit 241, an optional capture device 245, an input/output device(s) 247, optional sensor(s) 249, and a data storage 243, according to some examples. The components of the computing device 200 are communicatively coupled by a bus 220. In some implementations, the computing device 200 may be representative of the client device 115, the integrated healthcare server 120, or a combination of the client device 115 and the integrated healthcare server 120. In such implementations where the computing device 200 is the client device 115 or the integrated healthcare server 120, it should be understood that the client device 115 and the integrated healthcare server 120 may take other forms and include additional or fewer components without departing from the scope of the present disclosure. For example, while not shown, the computing device 200 may include sensors, additional processors, and other physical configurations. Additionally, it should be understood that the computer architecture depicted in FIG. 2A could be applied to other entities of the system 100 with various modifications, including, for example, the servers 140 and data sources 135.

The processor 235 may execute software instructions by performing various input/output, logical, and/or mathematical operations. The processor 235 may have various computing architectures to process data signals including, for example, a complex instruction set computer (CISC) architecture, a reduced instruction set computer (RISC) architecture, and/or an architecture implementing a combination of instruction sets. The processor 235 may be physical and/or virtual, and may include a single processing unit or a plurality of processing units and/or cores. In some implementations, the processor 235 may be capable of generating and providing electronic display signals to a display device 239, supporting the display of images, capturing and transmitting images, and performing complex tasks including various types of feature extraction and sampling. In some implementations, the processor 235 may be coupled to the memory 237 via the bus 220 to access data and instructions therefrom and store data therein. The bus 220 may couple the processor 235 to the other components of the computing device 200 including, for example, the memory 237, the communication unit 241, the display device 239, the input/output device(s) 247, the sensor(s) 249, and the data storage 243.

The memory 237 may store and provide access to data for the other components of the computing device 200. The memory 237 may be included in a single computing device or distributed among a plurality of computing devices as discussed elsewhere herein. In some implementations, the memory 237 may store instructions and/or data that may be executed by the processor 235. The instructions and/or data may include code for performing the techniques described herein. For example, as depicted in FIG. 2A, the memory 237 may store the integrated healthcare application 110. The memory 237 is also capable of storing other instructions and data, including, for example, an operating system, hardware drivers, other software applications, databases, etc. The memory 237 may be coupled to the bus 220 for communication with the processor 235 and the other components of the computing device 200.

The memory 237 may include one or more non-transitory computer-usable (e.g., readable, writeable) device, a static random access memory (SRAM) device, a dynamic random access memory (DRAM) device, an embedded memory device, a discrete memory device (e.g., a PROM, FPROM, ROM), a hard disk drive, an optical disk drive (CD, DVD, Blu-ray™, etc.) mediums, which can be any tangible apparatus or device that can contain, store, communicate, or transport instructions, data, computer programs, software, code, routines, etc., for processing by or in connection with the processor 235. In some implementations, the memory 237 may include one or more of volatile memory and non-volatile memory. It should be understood that the memory 237 may be a single device or may include multiple types of devices and configurations.

The bus 220 may represent one or more buses including an industry standard architecture (ISA) bus, a peripheral component interconnect (PCI) bus, a universal serial bus (USB), or some other bus providing similar functionality. The bus 220 may include a communication bus for transferring data between components of the computing device 200 or between computing device 200 and other components of the system 100 via the network 105 or portions thereof, a processor mesh, a combination thereof, etc. In some implementations, the integrated healthcare application 110 and various other software operating on the computing device 200 (e.g., an operating system 107, device drivers, etc.) may cooperate and communicate via a software communication mechanism implemented in association with the bus 220. The software communication mechanism may include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication may be configured to be secure (e.g., SSH, HTTPS, etc.).

The display device 239 may be any conventional display device, monitor or screen, including but not limited to, a liquid crystal display (LCD), light emitting diode (LED), organic light-emitting diode (OLED) display or any other similarly equipped display device, screen or monitor. The display device 239 represents any device equipped to display user interfaces, electronic images, and data as described herein. In some implementations, the display device 239 may output display in binary (only two different values for pixels), monochrome (multiple shades of one color), or multiple colors and shades. The display device 239 is coupled to the bus 220 for communication with the processor 235 and the other components of the computing device 200. In some implementations, the display device 239 may be a touch-screen display device capable of receiving input from one or more fingers of a user. For example, the display device 239 may be a capacitive touch-screen display device capable of detecting and interpreting multiple points of contact with the display surface. In some implementations, the computing device 200 (e.g., client device 115) may include a graphics adapter (not shown) for rendering and outputting the images and data for presentation on display device 239. The graphics adapter (not shown) may be a separate processing device including a separate processor and memory (not shown) or may be integrated with the processor 235 and memory 237.

The input/output (I/O) device(s) 247 may include any standard device for inputting or outputting information and may be coupled to the computing device 200 either directly or through intervening I/O controllers. In some implementations, the input device 247 may include one or more peripheral devices. Non-limiting example I/O devices 247 include a touch screen or any other similarly equipped display device equipped to display user interfaces, electronic images, and data as described herein, a touchpad, a keyboard, a scanner, a stylus, an audio reproduction device (e.g., speaker), a microphone array, a barcode reader, an eye gaze tracker, a sip-and-puff device, and any other I/O components for facilitating communication and/or interaction with users. In some implementations, the functionality of the input/output device 247 and the display device 239 may be integrated, and a user of the computing device 200 (e.g., client device 115) may interact with the computing device 200 by contacting a surface of the display device 239 using one or more fingers. For example, the user may interact with an emulated (i.e., virtual or soft) keyboard displayed on the touch-screen display device 239 by using fingers to contact the display in the keyboard regions.

The capture device 245 may be operable to capture an image (e.g., an RGB image, a depth map), a video or data digitally of an object of interest. For example, the capture device 245 may be a high definition (HD) camera, a regular 2D camera, a multi-spectral camera, a structured light 3D camera, a time-of-flight 3D camera, a stereo camera, a standard smartphone camera, a barcode reader, an RFID reader, etc. The capture device 245 is coupled to the bus to provide the images and other processed metadata to the processor 235, the memory 237, or the data storage 243. It should be noted that the capture device 245 is shown in FIG. 2A with dashed lines to indicate it is optional. For example, where the computing device 200 is the integrated healthcare server 120, the capture device 245 may not be part of the system, where the computing device 200 is the client device 115 or the medical device 145, the capture device 245 may be included and used to provide images, video and other metadata information described below.

The sensor(s) 249 includes any type of sensors suitable for the computing device 200. The sensor(s) 249 are communicatively coupled to the bus 220. In the context of the client device 115, the sensor(s) 249 may be configured to collect any type of signal data suitable to determine characteristics of its internal and external environments. Non-limiting examples of the sensor(s) 249 include various optical sensors (CCD, CMOS, 2D, 3D, light detection and ranging (LiDAR), cameras, etc.), audio sensors, motion detection sensors, magnetometer, barometers, altimeters, thermocouples, moisture sensors, infrared (IR) sensors, radar sensors, other photo sensors, gyroscopes, accelerometers, geo-location sensors, orientation sensor, wireless transceivers (e.g., cellular, Wi-Fi™, near-field, etc.), sonar sensors, ultrasonic sensors, touch sensors, proximity sensors, distance sensors, microphones, etc. In some implementations, the sensor(s) 249 may include one or more image sensors (e.g., optical sensors) configured to record images including video images and still images, may record frames of a video stream using any applicable frame rate, and may encode and/or process the video and still images captured using any applicable methods. In some implementations, the image sensor(s) 249 may capture images of surrounding environments within their sensor range. For example, in the context of a client device 115, the sensors 249 may capture the environment around the client device 115 including people, ambient light (e.g., day or night time), ambient sound, etc. In some implementations, the functionality of the capture device 245 and the sensor(s) 249 may be integrated. It should be noted that the sensor(s) 249 is shown in FIG. 2A with dashed lines to indicate it is optional. For example, where the computing device 200 is the integrated healthcare server 120, the sensor(s) 249 may not be part of the system, where the computing device 200 is the client device 115 or the medical device 145, the sensor(s) 249 may be included.

The communication unit 241 is hardware for receiving and transmitting data by linking the processor 235 to the network 105 and other processing systems via signal line 104 for example for the integrated healthcare server 120. The communication unit 241 receives data such as requests from the client device 115 and transmits the requests to the integrated healthcare application 110, for example a request to view an upcoming appointment with a health care provider. The communication unit 241 also transmits information including media to the client device 115 for display, for example, in response to the request. The communication unit 241 is coupled to the bus 220. In some implementations, the communication unit 241 may include a port for direct physical connection to the client device 115 or to another communication channel. For example, the communication unit 241 may include an RJ45 port or similar port for wired communication with the client device 115. In other implementations, the communication unit 241 may include a wireless transceiver (not shown) for exchanging data with the client device 115 or any other communication channel using one or more wireless communication methods, such as IEEE 802.11, IEEE 802.16, Bluetooth® or another suitable wireless communication method.

In yet other implementations, the communication unit 241 may include a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still other implementations, the communication unit 241 may include a wired port and a wireless transceiver. The communication unit 241 also provides other conventional connections to the network 105 for distribution of files and/or media objects using standard network protocols such as TCP/IP, HTTP, HTTPS, and SMTP as will be understood to those skilled in the art.

The data storage 243 is a non-transitory memory that stores data for providing the functionality described herein. In some implementations, the data storage 243 may be coupled to the components 235, 237, 239, 241, 245, 247, and 249 via the bus 220 to receive and provide access to data. In some implementations, the data storage 243 may store data received from other elements of the system 100 including, for example, entities 135, 140, 145, and/or the integrated healthcare applications 110, and may provide data access to these entities. The data storage 243 may store, among other data, user profiles 222, training datasets 224, machine learning models 226, clinical data 228, retail pharmacy data 230, and social and demographic data 232. The data storage 243 stores data associated with managing a health risk and medication adherence of a patient and other functionality as described herein. The data stored in the data storage 243 is described below in more detail.

The data storage 243 may be included in the computing device 200 or in another computing device and/or storage system distinct from but coupled to or accessible by the computing device 200. The data storage 243 may include one or more non-transitory computer-readable mediums for storing the data. In some implementations, the data storage 243 may be incorporated with the memory 237 or may be distinct therefrom. The data storage 243 may be a dynamic random access memory (DRAM) device, a static random access memory (SRAM) device, flash memory, or some other memory devices. In some implementations, the data storage 243 may include a database management system (DBMS) operable on the computing device 200. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations. In other implementations, the data storage 243 also may include a non-volatile memory or similar permanent storage device and media including a hard disk drive, a CD-ROM device, a DVD-ROM device, a DVD-RAM device, a DVD-RW device, a flash memory device, or some other mass storage device for storing information on a more permanent basis.

It should be understood that other processors, operating systems, sensors, displays, and physical configurations are possible.

As depicted in FIG. 2A, the memory 237 may include the integrated healthcare application 110.

In some implementations, the integrated healthcare application 110 may include a data processing engine 202, a machine learning engine 204, a total health index engine 206, a condition management engine 208, an adherence engine 210, and a user interface engine 212. The components 202, 204, 206, 208, 210, and 212 may be communicatively coupled by the bus 220 and/or the processor 235 to one another and/or the other components 237, 239, 241, 243, 245, 247, and 249 of the computing device 200 for cooperation and communication. The components 202, 204, 206, 208, 210, and 212 may each include software and/or logic to provide their respective functionality. In some implementations, the components 202, 204, 206, 208, 210, and 212 may each be implemented using programmable or specialized hardware including a field-programmable gate array (FPGA) or an application-specific integrated circuit (ASIC). In some implementations, the components 202, 204, 206, 208, 210, and 212 may each be implemented using a combination of hardware and software executable by the processor 235. In some implementations, each one of the components 202, 204, 206, 208, 210, and 212 may be sets of instructions stored in the memory 237 and configured to be accessible and executable by the processor 235 to provide their acts and/or functionality. In some implementations, the components 202, 204, 206, 208, 210, and 212 may send and receive data, via the communication unit 241, to and from one or more of the client devices 115, the medical devices 145, the integrated healthcare server 120, the data sources 135, and third-party servers 140.

The data processing engine 202 may include software and/or logic to provide functionality for receiving and processing a stream of data received from one or more entities of the system 100. For example, the stream of data may correspond to a plurality of users, such as patient members, physicians, clinical staff, administrative staff, etc. at one or more health care provider organizations. The data processing engine 202 receives a first stream of user-generated data from one or more data channels or engagement channels. For example, a data channel may be associated with one or more of the client device 115 and the medical device 145. User-generated data collected from different data channels may include, but is not limited to, data collected from one or more of user interactions and user preferences on a mobile application (e.g., email, messaging, social networking, media sharing, etc.) running on a smartphone, a proprietary web or cloud application running on a computer in a health care provider's office, a user wearable computing device tracking vital signs of a patient member, a medical device 145 monitoring health status information (e.g., heart rate, blood pressure, etc.) of a patient member, media content consumption history, feedback data (e.g., search, click-through, duration, ratings, reviews, etc.), various cloud services 111 (e.g., sleep quality data from a web API of a wearable sleep tracking device, physical activity data of the user from a web API of a fitness tracker device, calories and nutritional data from a web API of a calorie counter application, location check-in data from a web API of a location-based application, a calendar schedule of a user from a web API of a calendar application, social network contacts of a user from a web API of a social networking application, purchase history data from a web API of an e-commerce application, exercise log of workout routines, cycling statistics, running statistics, marathon participation statistics, 5K run, etc. from a web API of a fitness application, etc.) on the plurality of third-party servers 140 that are connected over the network 105 to the client devices 115 and medical devices 145, etc.

The data processing engine 202 receives a second stream of health or clinical data associated with the plurality of users. The data processing engine 202 receives a third stream of retail pharmacy data associated with the plurality of users. For example, the data processing engine 202 may query the plurality of data sources 135 for collecting the clinical data and the retail pharmacy data. Clinical data may include, but is not limited to, EMR data, EHR data, patient-physician encounter data (e.g., name, age, phone number, temperature, pulse, weight, height, encounter date, encounter type, encounter reason, encounter location, encounter time, encounter notes, etc.), patient demographics (e.g., gender, birth date, address, preferred language, ethnicity, marital status, religion, etc.), zip-code level demographics data, individual social determinant data (e.g., financial information, education level, mobility, race, alcohol use, tobacco use, drug use, etc.), patient surveys, patient problem list, patient procedures (e.g., ICD procedure codes, procedure date, procedure results, etc.), physician appointment history, upcoming appointment data, patient diagnoses, medical laboratory test results data, hospitalization data, rehabilitation data, health plan data, Center for Medicare & Medicaid Services Hierarchical Condition Category (CMS-HCC) risk score, census data and other public data (e.g., geography-level), etc. Pharmacy data may include, but is not limited to, prescription data, medication data (e.g., medication ID, date ordered, start and end date, etc.), pharmaceutical data, medication history, medication refills (e.g., number of refills, etc.), medication adherence data, proportion of days covered (PDC) score, polypharmacy data, drug interaction data, drug dosage, etc.

The data processing engine 202 processes, correlates, integrates, and synchronizes the received data streams from disparate devices 115, 145 and data sources 135 into a consolidated data stream as described herein. In some implementations, the data processing engine 202 instantiates a data ingestion layer that transports data from assorted data sources 135 to data storage 243 where it can be stored, accessed, and analyzed by the integrated healthcare application 110. For example, the data ingestion layer processes incoming data, prioritizes sources, validates individual files, and routes the data to the data storage 243. In some implementations, the data processing engine 202 instantiates a data transformation layer that maps and converts data from a source format (e.g., of a data source 135) to a destination format. For example, the data transformation layer transforms non-XML data to XML data. The data processing engine 202 creates a user profile 222 for a patient member based on processing the received data streams. The user profile 222 may include data and insights about the user including name, unique user identifier, age, gender, interests, height, weight, risk score, location, profile photo, recently measured vital signs, diagnosed conditions (e.g., diabetic, mental health, etc.), medical history, user preferences (e.g., phone call for upcoming reminders, soliciting information on stress management, etc.), prescription (e.g., refill dates, etc.), laboratory test results, fitness goals (e.g., gain physical mobility, lose weight, etc.), activities (e.g. number of physical therapy sessions, number of missed appointments, synced wearable fitness devices, synced third-party mobile Health Applications, etc.), etc. The data processing engine 202 stores and updates the user profiles 222 in the data storage 243.

In some implementations, the data processing engine 202 curates one or more training datasets 224 based on the data streams received in association with a plurality of the client devices 115, the medical devices 145, the third-party servers 140, and the data sources 135. The machine learning engine 204 described in detail below uses the training datasets 224 to train the machine learning models for performing the various functionality as described herein. Example training datasets 224 curated by the data processing engine 202 may include, but not limited to, a dataset containing historical embedding of medical and encounter history, details of next appointment, counts of previously missed appointments, and count of chronic conditions for a number of patient members with a labelled missed or cancelled appointment as outcome to predict, a dataset containing a set of content items and a set of user feedback (e.g., implicit feedback, such as viewing a content item, time spent on viewing the content item, searching for the content item, adding the content item to a wish list, etc. and/or explicit user feedback, such as rating on a scale of 1 to 5, likes, dislikes, reviews, etc.) given by the set of users about the set of content items, a dataset containing patient risk scores, social determinants, patient procedures, zip-code level demographics data, and medications for a number of patient members, etc. In some implementations, the data processing engine 202 may create a crowd-sourced training dataset 224. For example, in the instance where a user (e.g., patient member) consents to use of their data for creating a training dataset, the data processing engine 202 forwards the aggregated data to remotely located reviewers to review the data, identify a segment of the data, classify and provide a label for the identified data segment. The data processing engine 202 stores the curated training datasets 224 in the data storage 243.

The machine learning engine 204 may include software and/or logic to provide functionality for training one or more machine learning models 226 or classifiers using the training datasets created or aggregated by the data processing engine 202. The machine learning engine 204 is adapted to receive input from data scientists, analysts, or engineering staff to define and enhance the machine learning models 226. The machine learning engine 204 may also provide a portal through which these users can provide refinements and improvements to the models or introduce new models. In some implementations, the machine learning engine 204 receives and/or generates data, models, training data, and scoring parameters necessary to create the machine learning models 226. For example, the machine learning engine 204 may provide curated data inputs, provide label identification hints and patterns, provide model negators, perform training, testing, approval and publish model versions, perform scoring model parameter tuning, or create scoring accuracy thresholds.

In some implementations, the machine learning engine 204 may be configured to incrementally adapt and train the one or more machine learning models every threshold period of time. For example, the machine learning engine 204 may incrementally train the machine learning models every hour, every day, every week, every month, etc. based on the aggregated dataset. In some implementations, a machine learning model 226 is a neural network model and includes a layer and/or layers of memory units where memory units each have corresponding weights. A variety of neural network models may be utilized including feed forward neural networks, convolutional neural networks, recurrent neural networks, radial basis functions, other neural network models, as well as combinations of several neural networks. Additionally, or alternatively, the machine learning model 226 may represent a variety of other machine learning techniques in addition to neural networks, for example, support vector machines, decision trees, Bayesian networks, random decision forests, k-nearest neighbors, linear regression, least squares, hidden Markov models, other machine learning techniques, and/or combinations of machine learning techniques. In some implementations, the machine learning engine 204 may train one or more machine learning models 226 to perform a single machine learning task or a variety of machine learning tasks. In other implementations, the machine learning model 226 may be trained to perform multiple tasks.

The machine learning engine 204 determines a plurality of training instances or samples from the labelled dataset curated by the data processing engine 202. The machine learning engine 204 may apply a training instance as input to a machine learning model 226. In some implementations, the machine learning engine 204 may train the machine learning model 226 using any one of at least one of supervised learning (e.g., support vector machines, neural networks, logistic regression, linear regression, stacking, gradient boosting, etc.), unsupervised learning (e.g., clustering, neural networks, singular value decomposition, principal component analysis, etc.), or semi-supervised learning (e.g., generative models, transductive support vector machines, etc.). Additionally, or alternatively, machine learning models 226 in accordance with some implementations may be deep learning networks including recurrent neural networks, convolutional neural networks (CNN), networks that are a combination of multiple networks, etc. The machine learning engine 204 may generate a predicted machine learning model output by applying training input to the machine learning model 226. Additionally, or alternatively, the machine learning engine 204 may compare the predicted machine learning model output with a known labelled output from the training instance and, using the comparison, update one or more weights in the machine learning model 226. In some implementations, the machine learning engine 204 may update the one or more weights by backpropagating the difference over the entire machine learning model 226.

In some implementations, the machine learning engine 204 may test a trained machine learning model 226 and update it accordingly. The machine learning engine 204 may partition the labelled dataset obtained from the data processing engine 202 into a testing dataset and a training dataset. The machine learning engine 204 may apply a testing instance from the training dataset as input to the trained machine learning model 226. A predicted output generated by applying a testing instance to the trained machine learning model 226 may be compared with a known output for the testing instance to update an accuracy value (e.g., an accuracy percentage) for the machine learning model 226. Once a model 226 is trained and tested, the model is then published and made available for turning predictions. In some implementations, the model 226 may be versioned and serviced through an internal HTTP endpoint to be used by other component(s) of the integrated healthcare application 110. In some implementations, model training, testing and publishing will be iterative, and adapted automatically. New versions will be published based on improvements based on training of historical data and efficiency calculations as more data is collected over a period of time. The total health index engine 206 may include software and/or logic to provide functionality for determining a total health index score of a patient member. For example, the total health index score may be used to determine and recommend an actionable intervention to manage a health risk associated with the patient member.

Figure 2B:
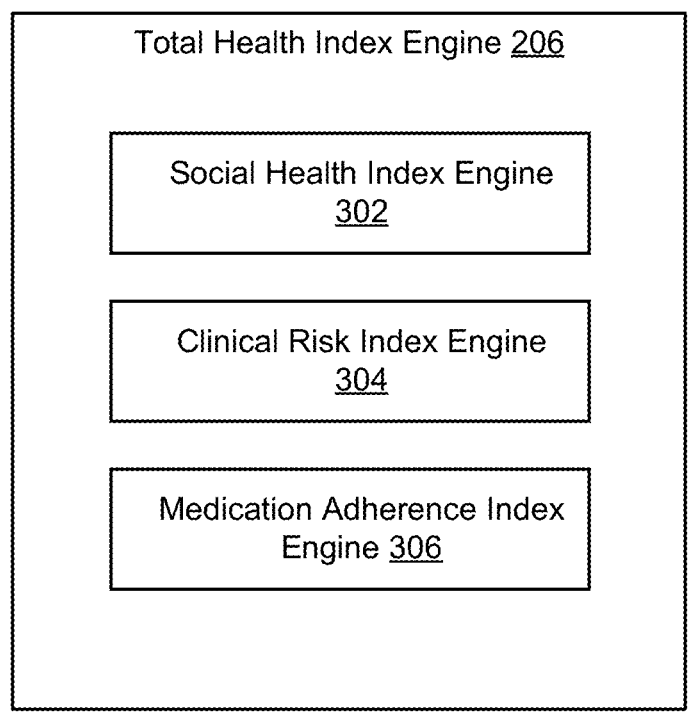
FIG. 2B is a block diagram illustrating one implementation of a total health index engine.

FIG. 2B is a block diagram illustrating an example implementation of a total health index engine 206. As depicted, the total health index engine 206 may include a social health index engine 302, a clinical risk index engine 304, and a medication adherence index engine 306, although it should be understood that the total health index engine 206 may include additional components. In some implementations, the total health index engine 206 may include two or more of the social health index engine 302, the clinical risk index engine 304, and the medication adherence index engine 306. The components 302, 304, and 306 may be communicatively coupled by the bus 220 and/or the processor 235 to one another and/or the other components 237, 239, 241, 243, 245, 247, and 249 of the computing device 200 for cooperation and communication. The components 302, 304, and 306 may each include software and/or logic to provide their respective functionality. In some implementations, the components 302, 304, and 306 may each be implemented using programmable or specialized hardware including a field-programmable gate array (FPGA) or an application-specific integrated circuit (ASIC). In some implementations, the components 302, 304, and 306 may each be implemented using a combination of hardware and software executable by the processor 235. In some implementations, each one of the components 302, 304, and 306 may be sets of instructions stored in the memory 237 and configured to be accessible and executable by the processor 235 to provide their acts and/or functionality. Each one of the components 302, 304, and 306 may be configured to implement one or more machine learning models 226 trained by the machine learning engine 204 to execute their functionality as described herein. The components 302, 304, and 306 may be configured to execute in parallel or in sequence. Each one of the components 302, 304, and 306 may be configured to transmit their generated results or output scores to the other components of the integrated healthcare application 110 for performing the functionality as described herein.

The social health index engine 302 receives the processed stream of user-generated data associated with different data channels of the user from the data processing engine 202. For example, the user-generated data may track the user's engagement with different mediums, such as their use of health and activity tracking devices, user activity on social media, changes in physical location based on their mobile devices, location check-ins into various restaurants or gyms, etc. In some implementations, the social health index engine 302 uses the user-generated data as input to one or more trained machine learning models to determine a social health index score for the user. For example, the social health index score of a patient is based on a quality of life and/or social health experienced by the patient. The social health index score measures an impact of the quality of life and/or social health of the patient on their physical health.

The clinical risk index engine 304 receives the processed stream of health and clinical contextual data of the user from the data processing engine 202. For example, the health and clinical contextual data may include EMR data, EHR data, patient-physician encounter data, appointment dates and times, types of appointments, rehabilitations and recoveries, etc. In some implementations, the clinical risk index engine 304 uses the health and clinical contextual data as input to one or more trained machine learning models to determine a clinical risk index score for the user. For example, the clinical risk index score is based on a probability of the patient missing an upcoming appointment with a health care provider and/or making a hospital visit in the near future.

The medication adherence index engine 306 receives a processed stream of pharmacy and medication contextual data of the user from the data processing engine 202. For example, the pharmacy and medication contextual data may include prescription data, medication history, polypharmacy (e.g., simultaneous user of multiple drugs), etc. In some implementations, the medication adherence index engine 306 uses the pharmacy and medication contextual data as input to one or more trained machine learning models to determine a medication adherence risk index score for the user. For example, the medication adherence risk score is based on how well or diligently the patient adheres to taking the prescribed medication for treating their health conditions.

The total health index engine 206 determines the total health index score based on incorporating one or more of the social health index score, the clinical risk index score, and the medication adherence index score. In some implementations, the total health index engine 206 determines an average of the social health index score, the clinical risk index score, and the medication adherence index score as the total health index score. In other implementations, the total health index engine 206 applies different weight values to each one of the social health index score, the clinical risk index score, and the medication adherence index score to determine the total health index score. For example, social health index score may be more heavily weighted than the clinical risk index score and the medication adherence index score in patients under the age of 35. In some implementations, the total health index engine 206 uses one or more trained machine learning algorithms to determine weight values for each of the social health index score, the clinical risk index score, and the medication adherence index score in the calculation of the total health index score. The total health index score of a patient is dynamic and the total health index engine 206 updates the total health index score over time based on one or more of the social health index score, the clinical risk index score, and the medication adherence index score changing and/or weighting of the various index scores changing as more data is collected over time and the machine learning models change based on the data collected. In some implementations, user specific actionable interventions and other services may be determined and recommended based on the total health index score to manage one or more health conditions for various users as described herein. The total health index score may take into account multiple health conditions that are present in a user. This allows the total health index score to be used to determine a specific actionable intervention than only if a single health condition were being analyzed and tracked. For example, the total health index score in conjunction with a user profile 222 may indicate the distance a user is from a hospital, a recent missed appointment, and a current health condition to determine a specific actionable intervention personalized for that user in order to manage their health condition, that would be different from another user that was closer to the hospital and not missing appointments.

Referring back to FIG. 2A, the remaining components of the integrated healthcare application 110a will be described. The condition management engine 208 may include software and/or logic to provide functionality to facilitate user management of one or more of their health conditions. Health conditions may include, for example, diabetes, pregnancy, osteoarthritis, cancer, mental health, chronic conditions, episodic conditions, etc. The condition management engine 208 uses the total health index score and diverse set of data about the user as input to one or more trained machine learning models to facilitate the user with managing their health conditions and risks. For example, the diverse set of data may include encounters, diagnoses, laboratory test results, user wearable device data, medication and refill history, user's application preferences, etc. The condition management engine 208 personalizes the user experience with condition management and generates personalized, real-time recommendations of actionable interventions. Example determinations made by the condition management engine 208 for improving health outcomes and managing health risks in patients may include, but are limited to, missed appointment predictions for generating escalating reminders, content recommendations (e.g., articles, videos, etc.) for knowledge building about health conditions and action to improve care outcomes, proactive and real-time communications for enabling behavioral change in users (e.g., medication adherence), identification of co-morbidities, condition progression analysis (e.g., pre-diabetic to diabetic, etc.) for reducing disease progression, and hospital utilization predictions for guiding health care providers in decision making.

In some implementations, the condition management engine 208 identifies patient members who are likely at risk of missing an upcoming scheduled appointment with a health care provider and determines an actionable intervention as recommendation for such patient members. The condition management engine 208 determines that the health risk is a likelihood of the user missing their next scheduled appointment with the health care provider. Example input data analyzed by the condition management engine 208 for predicting a risk of missed appointments may include, but are not limited to, encounter, diagnoses, procedures, problem list, encounter notes, medication data, demographic data, zip-level demographic data, etc. The condition management engine 208 uses a trained 'missed appointment' machine learning model on the input data for identifying a patient at risk of missing an appointment and intervening by sending an additional notification to the patient. For example, the 'missed appointment' model may be a binary classification model trained on a historical dataset containing features of previously scheduled patient-physician encounters, next appointment details, counts of previous missed appointments, counts of chronic conditions, demographic data, etc. of a number of users. The condition management engine 208 automatically sends a reminder notification to the identified patient at risk of missing their next appointment. The condition management engine 208 escalates with the reminder notifications as the scheduled appointment approaches. The condition management engine 208 identifies a medium or communication channel for sending the reminder notification based on the user preferences and a proximity of the upcoming scheduled appointment. For example, the condition management engine 208 selects email for sending a first reminder notification a month away from the scheduled appointment, selects text messaging for sending a second reminder notification a week away from the scheduled appointment, selects an automated phone call for sending a third reminder notification, etc.

The condition management engine 208 performs co-morbidity analysis to identify patient members who are at risk of developing a new disease or health condition given their current and/or existing diagnosis of another health condition. The condition management engine 208 determines that the health risk is a likelihood of a patient developing one or more co-morbidities and determines an actionable intervention for managing the health risk. Example input data analyzed by the condition management engine 208 for predicting a risk of developing co-morbidities may include, but are not limited to, diagnoses, individual social determinant data, problem list, laboratory tests and medication data, demographic data, and census and other public data. The condition management engine 208 facilitates a data analyst to segment the data to understand most frequently occurring multi-morbidity occurrences. The goal is to identify which diagnoses tend to appear together in a higher frequency than expected by chance. By analyzing association of each diagnosis with the rest, a co-morbidity network of associations between diagnoses can be built. In some implementations, the condition management engine 208 uses a temporal exponential-family random graph model (TERGM) for analyzing the data from co-morbidity network to identify co-occurring patterns. For example, the condition management engine 208 analyzes patient procedures and medications, CMS-HCC risk score, co-morbidity indices, social determinants, and zip-code level variables to detect a likelihood of co-morbidities developing in a patient. The condition management engine 208 creates and conveys personalized risk propensities for the patient. The condition management engine 208 generates a notification for a health care provider of the patient to open discussion on multi-morbidities with their patients identified being at risk. The condition management engine 208 automatically generates a suggestion of scheduling an appointment for medically testing for a disease associated with the co-morbidity that appears highly correlated with the patient's problem list. Once the suggestion is accepted by the patient and/or the health care provider, the condition management engine 208 automatically schedules and creates the appointment.

The condition management engine 208 generates content recommendations for patients diagnosed with a health condition. The content recommendations are aimed at engaging the patient members diagnosed with a health condition, for example, a chronic disease, such as diabetes, etc. and pursue an action in managing their health condition. The condition management engine 208 determines that the health risk is a likelihood of a health condition progressing in a patient and generates content recommendations for user's consideration. For example, content recommendation may be in the form of articles, videos, and other media to support the patients to take positive actions (e.g., follow diet and recipes, perform exercise movements, join emotional and social support groups, etc.) and stay in control of their health condition. The condition management engine 208 uses a trained recommender model implementing collaborative filtering algorithm for generating content recommendations. Data including a set of content items and a set of feedback (e.g., implicit feedback, such as viewing a content item, time spent on viewing the content item, searching for the content item, adding the content item to a wish list, etc. and/or explicit feedback, such as rating on a scale of 1 to 5, likes, dislikes, reviews, etc.) given by the set of users about the set of content items, contextual user device data (e.g., fitness tracker, smartphone, smartwatch, etc.), and patient EHR data, etc. are fed into the trained recommender model by the condition management engine 208 to generate one or more of the user based recommendations (similarity between users) and the item based recommendations (similarity between items). For example, the condition management engine 208 uses the common attributes between the patient members to generate content recommendations.

Figure 3A:
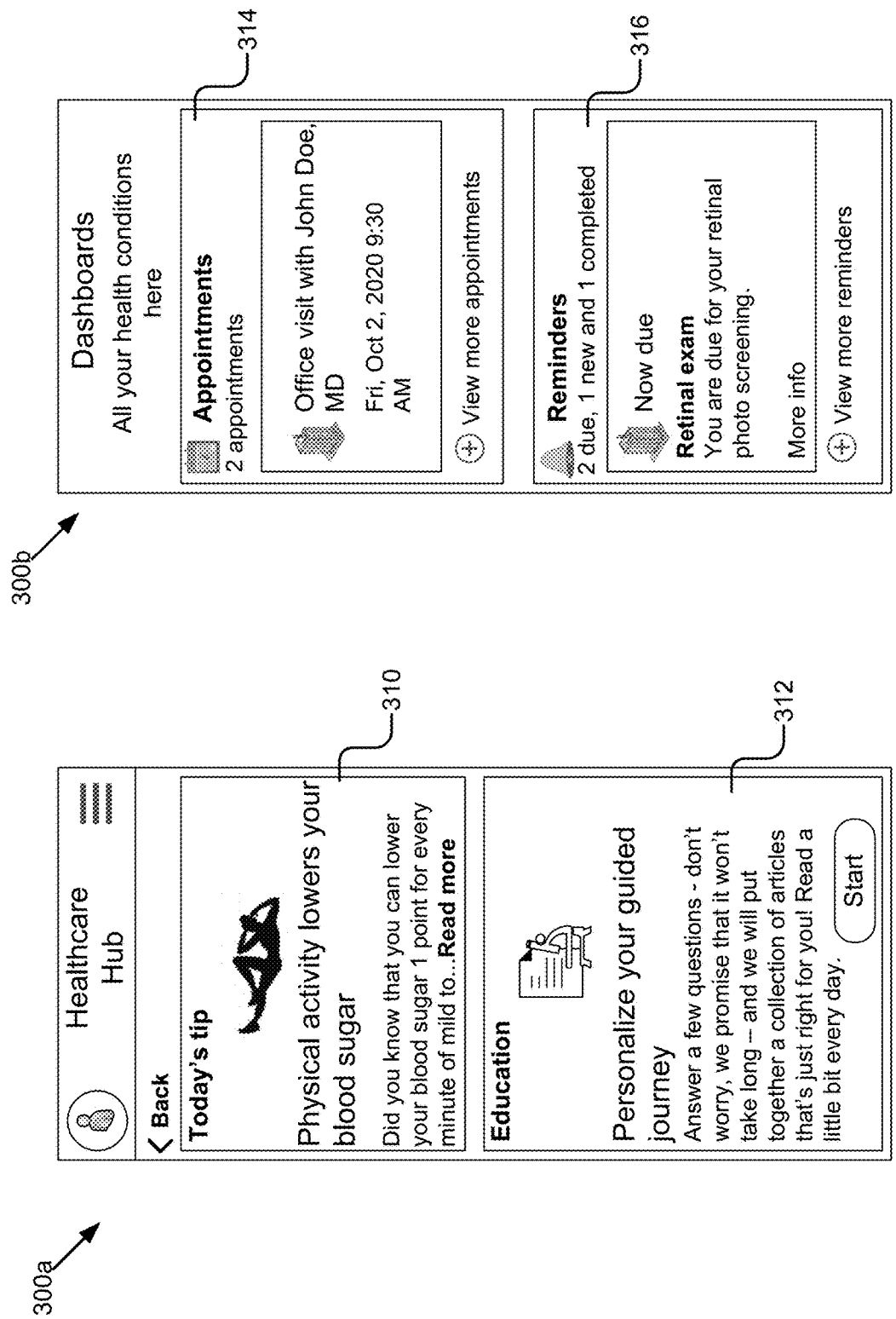

The condition management engine 208 generates a dashboard for providing condition management to a user. The user experience associated with the dashboard for condition management includes a convenient presentation of key protected health information (PHI) indicators and status (e.g., prescription medication, annual physical exam appointments, laboratory tests, wellness mobile applications, etc.) of the specific user, educational content recommendations (e.g., article about controlling blood sugar level, etc.) for a specific diagnosed condition of the user, user health goals and to-do lists, medication planning and reminders, appointment management, emotional and social support groups, etc. FIGS. 3A-3B show example graphical representations illustrating user interfaces 300a-300d for presenting a dashboard for condition management to a user. The user interfaces 300a-300d may be presented on a mobile application running on a client device 115, such as a mobile computing device. Although the user interfaces 300a-300d are shown split, they may be scrolled through in sequence on a display of the mobile computing device. The dashboard for condition management is designed to provide the user with timely access to tools, educational resources, and care or wellness teams. The dashboard for condition management is personalized to the patient member viewing the dashboard. In FIG. 3A, the user interface 300a shows a first portion 310 for a daily tip and a second portion 312 for an educational article that are personalized to the user's diagnosis. In FIG. 3A, the user interface 300b shows a third portion 314 for upcoming appointments with health care providers and a fourth portion 316 for displaying reminders set by and/or for the patient. In one example, one user might receive the reminders a day before a doctor's appointment, while another user may receive those reminders farther out. The reminder may include a deep link that is selectable by the user to view additional details, such as the address of the doctor's appointment. The reminder may indicate to the user to schedule a ride to the address of the doctor's appointment based on the distance from the health care provider and an age of the user. In FIG. 3B, the user interface 300c shows a fifth portion 318 detailing the user's medication (e.g., the user may be able to quickly review the medication availability for refill and number of refills remaining in the user's prescription), a sixth portion 320 for displaying laboratory test results, and a seventh portion 322 for contacting care team or wellness coach. In FIG. 3B, the user interface 300d shows an eighth portion 324 for wellness mobile applications that the user can get for free or a low cost.

The adherence engine 210 may include software and/or logic to provide functionality for identifying patient members at risk of non-adherence to their prescribed medication and determining one or more actionable interventions as a recommendation to improve medication adherence in the at-risk patient members. For example, an actionable intervention may be proactive rather than reactive, such as sending a reminder through text messaging to encourage timely refills of prescriptions by the patient member. In some implementations, the adherence engine 210 analyzes a diverse set of patient data including social determinants, behavioral data, user-generated data, device data, encounter data, pharmacy data, total health index score, medication adherence index score, diagnoses and problem list, procedures, encounter notes, etc. using one or more trained machine learning models to determine or predict a user's risk of non-adherence to medication and recommend an actionable intervention to manage the health risk of the user.

Example determinations made by the adherence engine 210 for prioritizing patient health and reducing complications from medication non-adherence may include, but are limited to, maximization analyses for various ratings (e.g., CMS rating or other healthcare ratings), member-level adherence predictions (e.g., identifying members who may be non-adherent), intervention recommendations (e.g., pre-emptive action via digital and warm touch interactions to encourage user understanding and action, etc.), side effect rulesets, identification of co-morbidities, hospital utilization predictions, and dashboard and report generation for supporting business decision making.

The adherence engine 210 prioritizes identifying high-acuity patient members with chronic disease conditions at risk of non-adherence to their prescribed medication. Prioritizing high-acuity patient members with chronic disease conditions can reduce hospitalization and emergency department (ED) visits and health care costs for the patient members caused by complications from medication non-adherence. Example chronic conditions may include heart failure, renal failure, uncontrolled diabetes, uncontrolled hypertension, chronic obstructive pulmonary disease, acute respiratory distress syndrome, etc. The adherence engine 210 identifies patient members at risk of non-adherence to certain medication categories (e.g., Statin, ACE inhibitors, diabetes medication, anticoagulants, blood pressure medication, etc.) used in treating and managing the chronic disease conditions for intervention.

The adherence engine 210 identifies patient members who are likely to have a medication adherence score (e.g., PDC score) below a certain threshold by the end of a predetermined period. The medication adherence score may be per patient and/or per medication. The end of the predetermined period may be one of the end of the month, the end of the quarter, the end of the year, etc. The threshold may be a value set by an industry standard, such as 0.8, below which a patient member is considered non-adherent. Example input data analyzed by the adherence engine 210 for predicting a likelihood of a patient member having a medication adherence score below a threshold may include, but are not limited to, encounter, diagnoses, procedures, problem list, encounter notes, medication data, demographic data, monthly PDC snapshot data, etc. The at-risk patient members to identify by the adherence engine 210 may belong to two separate groups: a first group of patient members with a PDC score (e.g., existing medication prescription) and a second group of patient members without a PDC score (e.g., new medication prescription).

The adherence engine 210 uses a first machine learning model (i.e., trained specifically for identifying at-risk members with a PDC score) using input of one or more PDC snapshot data and demographics data to predict a likelihood of a patient member having a PDC score below the threshold by the end of a predetermined period. For example, the first machine learning model may be a binary classification model trained using a dataset containing features of monthly PDC snapshot data and demographics data of a number of patient members. The adherence engine 210 uses a second machine learning model (i.e., trained specifically for identifying at-risk members without a PDC score) using input of one or more of medical and encounter history, medication and chronic condition count, and counts of previous missed appointments to predict a likelihood of a patient member having a PDC score below the threshold by the end of a predetermined period. For example, the second machine learning model may be a gradient boosted decision tree trained using a dataset containing features including medical and encounter history, medication and chronic condition count, and counts of previous missed appointments for a number of patient members at the moment they are prescribed a new medication.

The adherence engine 210 determines an actionable intervention to improve the medication adherence of a patient member identified to be at risk of non-adherence to medication. The adherence engine 210 uses one or more machine learning models on a set of patient member data to determine an actionable intervention that is optimal for the at-risk patient member. In one example, the actionable intervention may be a digital intervention, such as periodically sending a reminder to the patient member to pick up prescription through one or more of a phone call, text messaging, in-app notification messaging within a health care application, email, interactive voice response (IVR), sending a website hyperlink to the patient member for placing a prescription refill order for home delivery, curbside pickup, mail order, etc. In another example, the actionable intervention may be an educational intervention, such as electronically sending a comic strip to the patient member with a story about the benefits of adhering to taking medication, sending an article describing benefits of the prescribed medication in improving the lifestyle of people similar to the patient member, etc. In another example, the actionable intervention may be a social intervention, such as scheduling an appointment with a social worker for a counselling session, informing a family contact of the at-risk patient member to help with adherence, sending a reminder in a native language (e.g., Spanish) of the patient member with limited English proficiency, etc. The adherence engine 210 automatically initiates the actionable intervention. The adherence engine 210 aggregates data associated with the results of the actionable interventions on the medication adherence score for analysis. For example, the adherence engine 210 compares the patient member demographics by the medication adherence score.

The adherence engine 210 determines a population of patient members to target for one or more intervention campaigns. The adherence engine 210 may provide a decision support system portal for a team of health care professionals to define which population of patient members to target for an intervention campaign. For example, the population of patient members may be a group of users diagnosed with diabetes. In another example, the population of patient members may be a group of users having limited English proficiency. In yet another example, the population of patient members may be a group of users from a particular zip code. The adherence engine 210 divides the population of patient members into a test group and a control group. The adherence engine 210 identifies patient members at risk of non-adherence to their prescribed medication in the test group and determines one or more actionable interventions to improve medication adherence in the at-risk patient members. The adherence engine 210 aggregates data associated with the results of the actionable interventions from the campaign for analysis. The adherence engine 210 instructs the user interface engine 212 to generate one or more dashboard user interfaces for the team of health care professionals, researchers, and analyst to track improvements and effectiveness of the intervention campaign, identify patient members to contact with an actionable intervention, and facilitate with determining a next target group for a future intervention campaign.

The user interface engine 212 may include software and/or logic for providing user interfaces to a user. In some implementations, the user interface engine 212 receives instructions from the components 202, 204, 206, 208, and 210, generates a user interface according to the instructions, and transmits the user interface for display on the client device 115 as described above with reference to FIGS. 3A, 3B, and described below for FIGS. 4A, 4B, 5 and 6. In some implementations, the user interface engine 212 sends graphical user interface data to an application (e.g., a browser) in the client device 115 via the communication unit 241 causing the application to display the data as a graphical user interface.

Figure 4A:
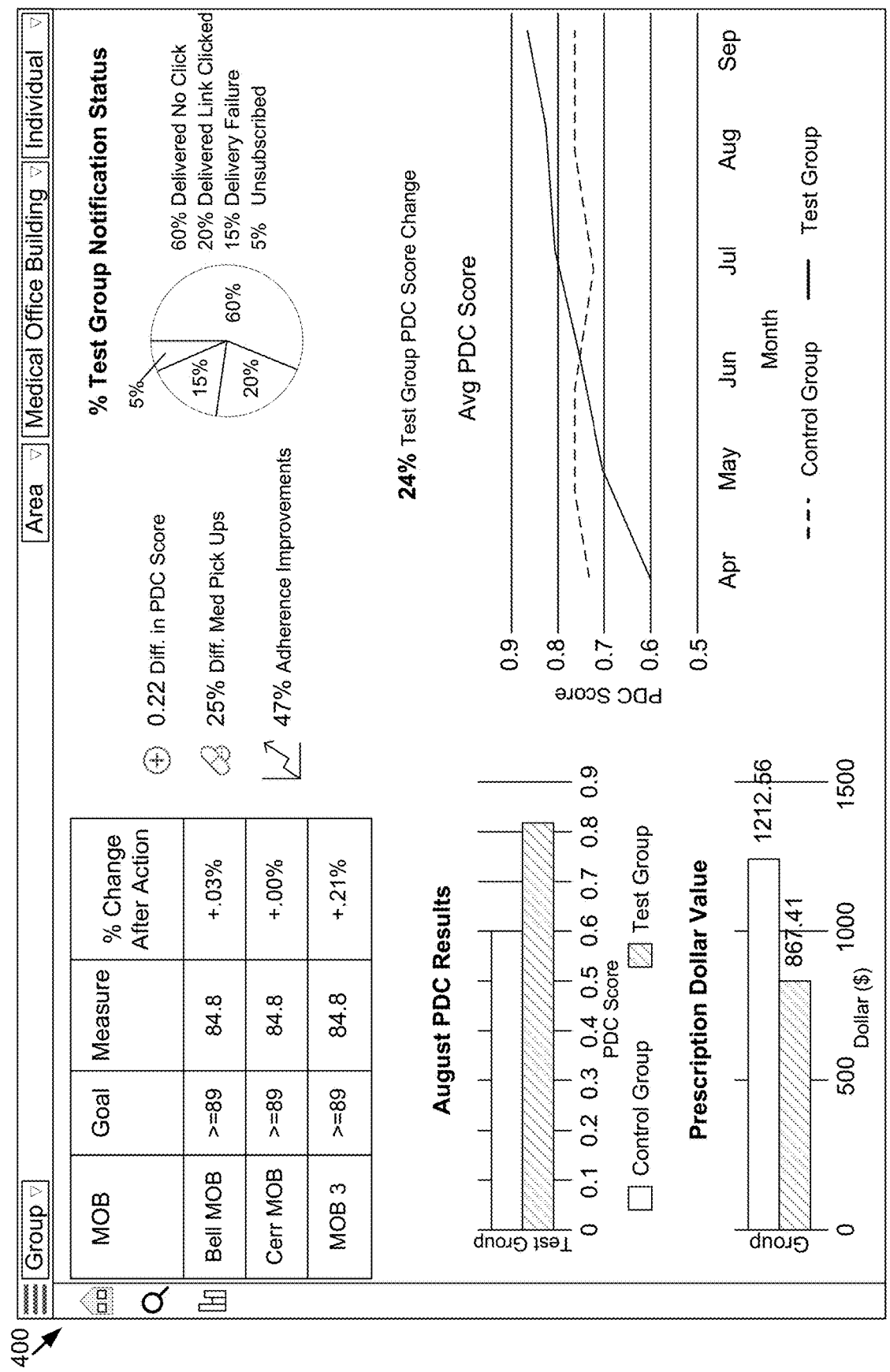
FIGS. 4A-4B show graphical representations of example user interfaces for a dashboard displaying the statistics of medication adherence intervention campaign according to some implementations.
Figure 4B:

FIGS. 4A-4B show example graphical representations of user interfaces for a dashboard displaying the statistics of medication adherence intervention campaign. In the FIG. 4A, the user interface 400 depicts a display of statistical graphs comparing the difference in medication adherence between a test group and a control group caused by the intervention campaign that is tracked over time. For example, the test group received reminder notification messages to pick up their prescription according to the one or more actionable interventions initiated and executed for the patient members in the test group. The control group did not receive any such reminder notification messages. The statistical graphs compare and contrast historical data to the results from the medication adherence intervention campaign. In FIG. 4B, the user interface 450 depicts a display of table. Each row in the table includes intervention details of a patient member in the test group who was contacted with a reminder notification (e.g., a text message notification to refill prescription) for medication adherence. Example data needed to generate the dashboard depicted in FIGS. 4A-4B include actual PDC score, medication 5-star rating, order type, prescription information (e.g., quantity, price), patient demographics (e.g., ethnicity, age, primary language, etc.), patient information (e.g., if they opened the notification message, time spent viewing the notification message, click through of a link in the notification message, etc.), etc.

FIG. 5 shows an example graphical representation of a user interface 500 for a dashboard identifying patient members to contact with an actionable intervention. In the FIG. 5, the user interface 500 depicts a table of patient member information who is to be contacted in the medication adherence intervention campaign. The user interface 500 of the dashboard may be presented to a pharmacy technician tasked with managing the administration of the intervention. For example, the pharmacy technician may review the list of patient members for whom the prescription refill date is approaching and select a number of patient members from the list with low medication adherence score and high-risk health condition to receive a reminder notification. The user interface 500 includes patient member contact information and a preferred language. The user interface 500 also includes where the patient member went to pick up the prescription order and the medication that the patient member uses. Example data needed to generate the dashboard depicted in FIG. 5 include age, full name, gender, primary language, limited English proficiency (LEP) status, medical record number (MRN), phone number, medical office building (MOB), MOB city, drug class, order type, prescription ID, prescription name, prescription refill date, outreach date, outreach status, outreach type, PDC score, etc.

Figure 6:
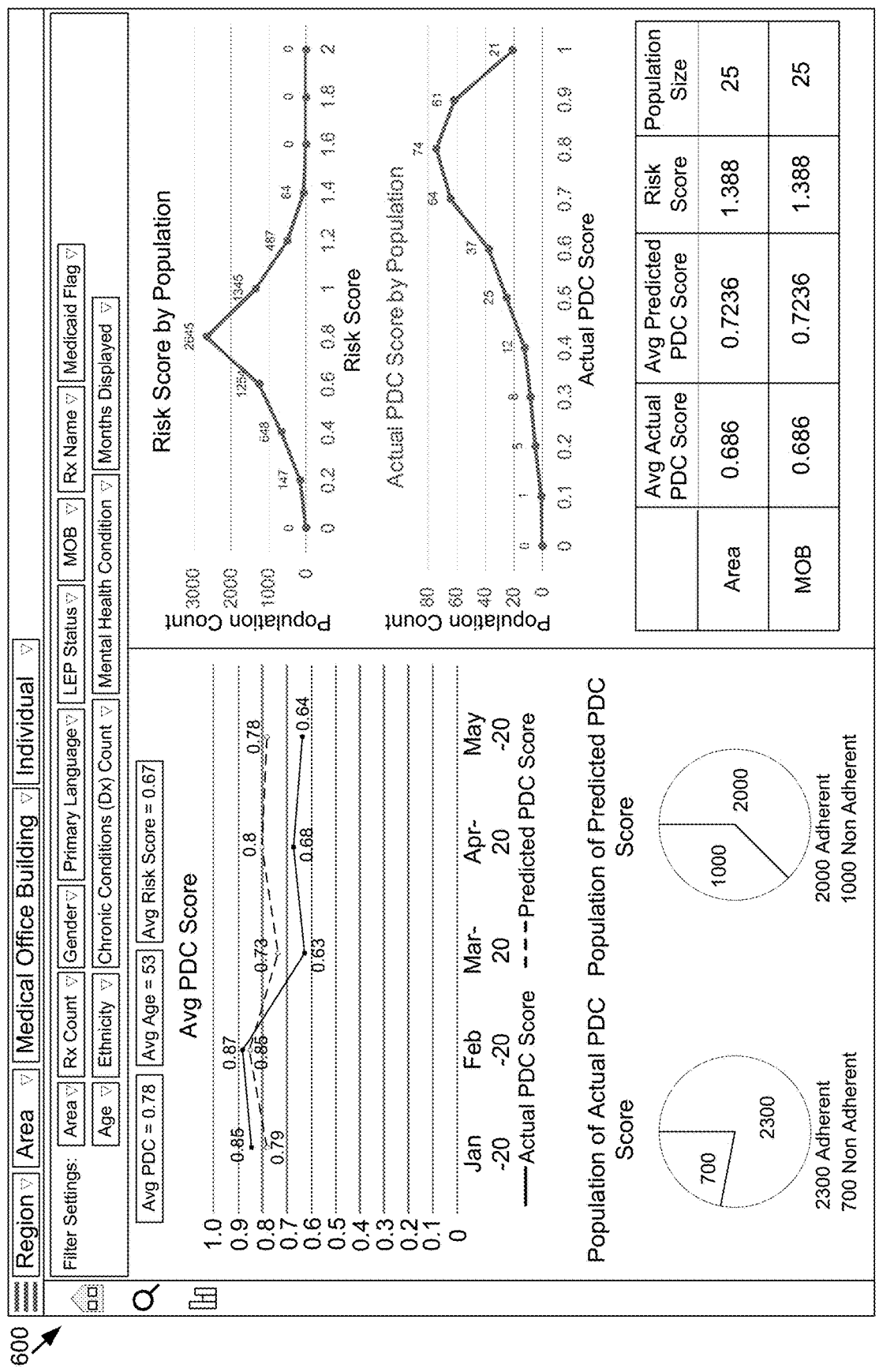
FIG. 6 shows a graphical representation of an example user interface for a dashboard to facilitate with determining a next target group for a future intervention campaign according to some implementations.

FIG. 6 shows an example graphical representation of a user interface 600 for a dashboard to facilitate with determining a next target group for a future intervention campaign. In FIG. 6, the user interface 600 shows that the results of the medication adherence campaign for all patient members can be filtered to analyze trends with multiple different factors, such as age, area, gender, prescription count, etc. The user interface 600 of the dashboard may be presented to a business decision support professional tasked with determining a group of patient members for a next round of intervention campaign. Example data needed to generate the dashboard depicted in FIG. 6 include age, gender, primary language, medical record number (MRN), medical office building (MOB), MOB city, drug class, order type, prescription name, etc.

Figure 7:
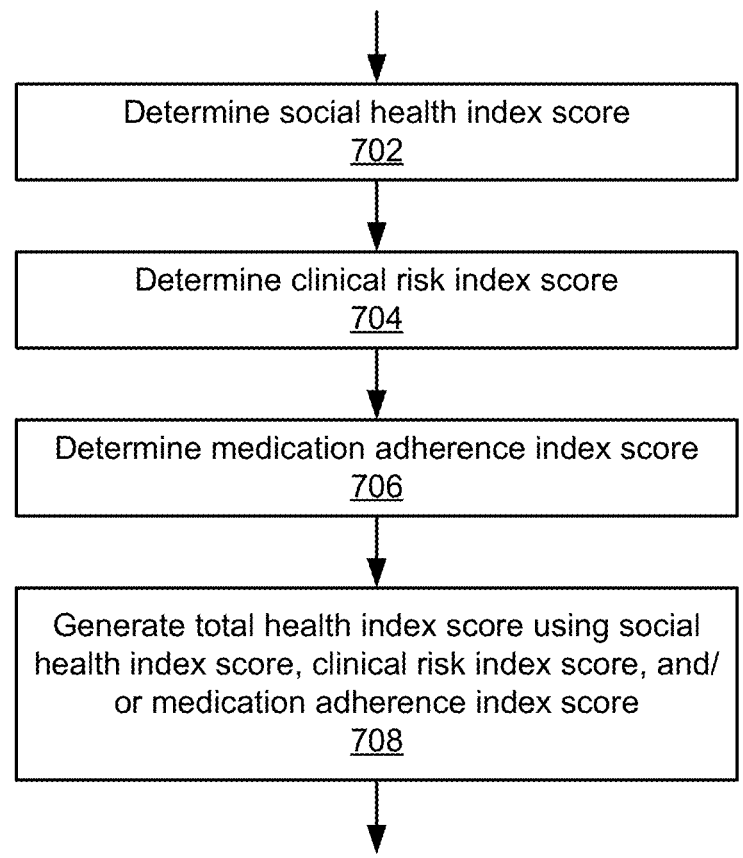
FIG. 7 is a flow diagram illustrating one implementation of an example method for generating a total health index.

FIG. 7 is a flow diagram of an example method 700 for generating a total health index. At 702, the social health index engine 302 may determine the social health index score by collecting data from various users, such as engagement data, and may analyze that data using various machine learning algorithms in order to determine the social health index score. At 704, the clinical risk index engine 304 may determine the clinical risk index score by collecting data from various healthcare organizations, such as provider data that includes appointments, doctor visits, hospital visits, etc., and may analyze that data using various machine learning algorithms in order to determine the clinical risk index score. At 706, the medication adherence index engine 306 may determine the medication adherence index score by collecting various medication related data of the user, such as drug prescriptions and/or medication history and may analyze that data using various machine learning algorithms in order to determine the medication adherence index score. The total health index engine 206 may then generate the total health index score using the social health index score, the clinical risk index score, and the medication adherence index score. The total health index engine 206 may use an average of each of the scores. In further implementations, the total health index engine 206 may use a weighted value for each of the scores to generate the total health index score. In some implementations, an artificial intelligence model may be used to calculate the different weights for each of the index scores.

Figure 8:
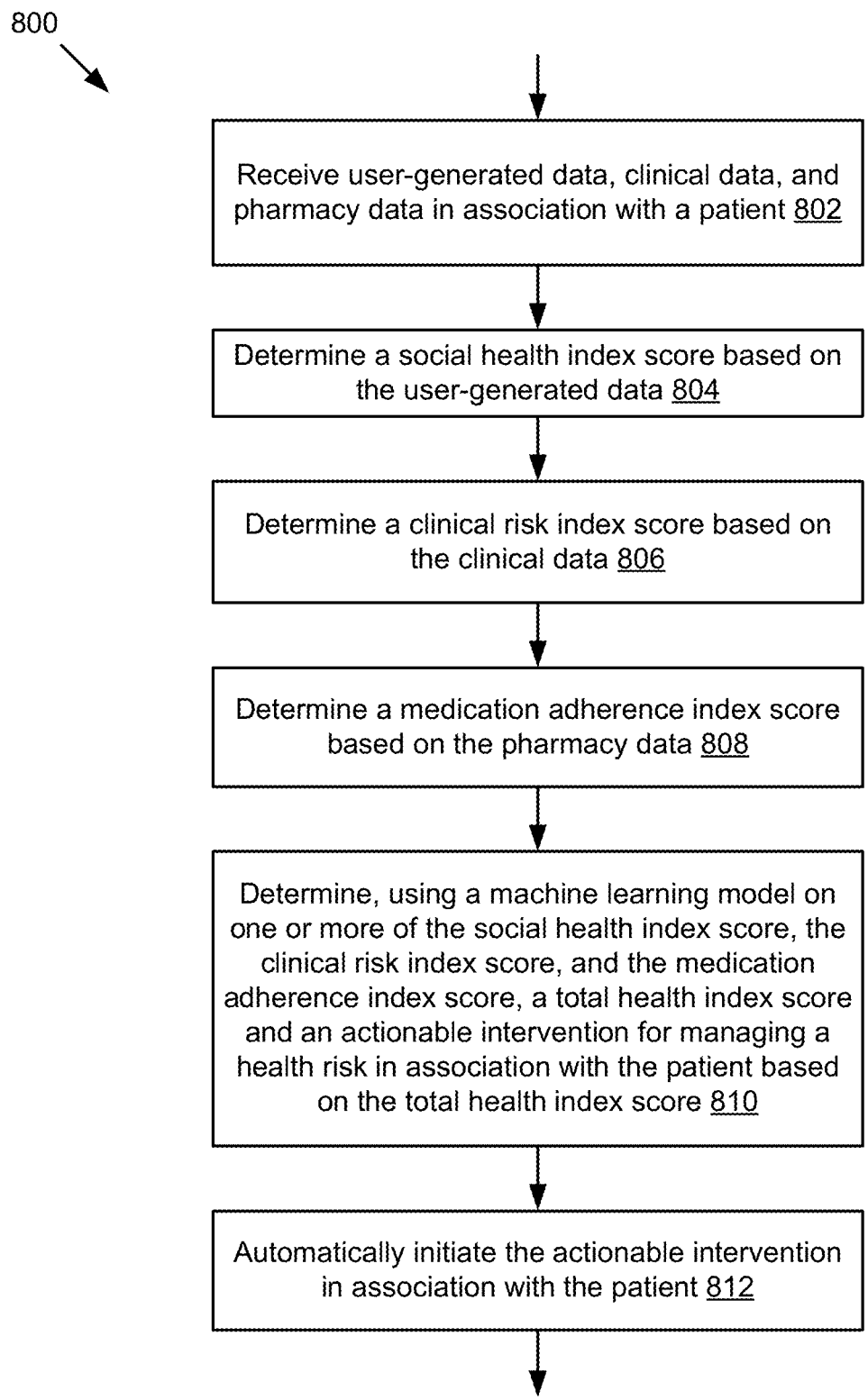
FIG. 8 is a flow diagram illustrating one implementation of an example method for generating a total health index and recommending an actionable intervention for managing a health risk of a patient.

FIG. 8 is a flow diagram illustrating one implementation of an example method 800 for generating a total health index and recommending an actionable intervention for managing a health risk of a patient. At 802, the data processing engine 202 receives user-generated data, clinical data, and pharmacy data in association with a patient. At 804, the social health index engine 302 determines a social health index score based on the user-generated data. At 806, the clinical risk index engine 304 determines a clinical risk index score based on the clinical data. At 808, the medication adherence index engine 306 determines a medication adherence index score based on the pharmacy data. At 810, the total health index engine 206 determines, using a machine learning model on one or more of the social health index score, the clinical risk index score, and the medication adherence index score, a total health index score and an actionable intervention for managing a health risk in association with the patient based on the total health index score. At 812, the adherence engine 210 automatically initiates the actionable intervention in association with the patient.

A system and method for generating a total health index and recommending an actionable intervention for managing a health risk of a patient has been described. In the above description, for purposes of explanation, numerous specific details are set forth in order to provide a thorough understanding of the techniques introduced above. It will be apparent, however, to one skilled in the art that the techniques can be practiced without these specific details. In other instances, structures and devices are shown in block diagram form in order to avoid obscuring the description and for ease of understanding. For example, the techniques are described in one implementation above primarily with reference to software and particular hardware. However, the present invention applies to any type of computing system that can receive data and commands, and present information as part of any peripheral devices providing services.

Reference in the specification to "one implementation" or "an implementation" means that a particular feature, structure, or characteristic described in connection with the implementation is included in at least one implementation. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are, in some circumstances, used by those skilled in the data processing arts to convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of a hardware implementation, a software implementation, or implementations containing both hardware and software elements. For instance, the technology may be implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies, engines, and other aspects of the disclosure can be implemented as software, hardware, firmware, or any combination of the foregoing. Also, wherever an element, an example of which is a module, of the specification is implemented as software, the element can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A computer-implemented method comprising:
receiving, using one or more processors, a user-generated dataset, a clinical dataset, and a pharmacy dataset in association with a plurality of patients;
training, using one or more processors, a machine learning model using a set of the user-generated dataset, the clinical dataset, and the pharmacy dataset in association with the plurality of patients, the set of the user-generated dataset, the clinical dataset, and the pharmacy dataset including known health risks of the plurality of patients to train the machine learning model, the machine learning model including a neural network of assigning a weight to different patient health index scores;
determining, using the one or more processors, a social health index score of a patient from the plurality of patients based on user-generated data associated with the patient in the user-generated dataset;
determining, using the one or more processors, a clinical risk index score of the patient based on clinical data associated with the patient in the clinical dataset;
determining, using the one or more processors, a medication adherence index score of the patient based on pharmacy data associated with the patient in the pharmacy dataset;
determining, using the machine learning model, a total health index score of the patient, the total health index score including a weighted combination of the social health index score, the clinical risk index score, and the medication adherence index score, the machine learning model assigning a weight to each of the social health index score, the clinical risk index score, and the medication adherence index score of the patient;
determining an actionable intervention for managing a health risk in association with the patient based on one or more of the total health index score, the user-generated data, the clinical data, and the pharmacy data of the patient; and
automatically initiating, using the one or more processors, the actionable intervention.

2. The computer-implemented method of claim 1, wherein determining the actionable intervention for managing the health risk in association with the patient further comprises:
determining, from an output of the machine learning model, that the health risk is a likelihood of the patient missing an upcoming healthcare appointment scheduled with a healthcare provider;
identifying a communication channel preferred by the patient; and
determining the actionable intervention to send an additional notification reminding the patient about the upcoming healthcare appointment through the identified communication channel.

3. The computer-implemented method of claim 1, wherein determining the actionable intervention for managing the health risk in association with the patient further comprises:
determining, from an output of the machine learning model, that the health risk is a likelihood of a health condition progressing in the patient; and
determining the actionable intervention to recommend content to the patient, the content associated with educating the patient about reducing a progression of the health condition.

4. The computer-implemented method of claim 1, wherein determining the actionable intervention for managing the health risk in association with the patient further comprises:
determining, from an output of the machine learning model, that the health risk is a likelihood of a comorbidity in the patient; and
determining the actionable intervention to schedule an appointment with a healthcare provider of the patient for medically testing a disease associated with the comorbidity in the patient.

5. The computer-implemented method of claim 1, wherein determining the actionable intervention for managing the health risk in association with the patient further comprises:
determining, from an output of the machine learning model, that the health risk is a likelihood of a medication adherence score of the patient being less than a threshold by end of a predetermined time period; and
determining the actionable intervention from a group of a digital intervention, an educational intervention, and a social intervention to facilitate the patient with adhering to taking their prescribed medication.

6. The computer-implemented method of claim 5, wherein the digital intervention includes sending a reminder notification through one or more of a phone call, text messaging, email, in-app messaging within a health care mobile application, and an interactive voice response.

7. The computer-implemented method of claim 5, wherein the educational intervention includes sending a comic strip including a story about a benefit associated with adhering to taking prescribed medication.

8. The computer-implemented method of claim 5, wherein the social intervention includes one or more of scheduling an appointment with a social work for a counseling session, informing a family member of the patient to help with medication adherence, and sending a reminder in a native language of the patient with limited English proficiency.

9. The computer-implemented method of claim 1, further comprising:
generating a dashboard for condition management, the dashboard providing access to one or more of protected health information indicators and status, educational content recommendations, medication planning and reminders, appointment management, and social and emotional support groups; and
presenting the dashboard for condition management to the patient.

10. The computer-implemented method of claim 1, further comprising:
    determining a population of patients to target for a medication adherence campaign;
    dividing the population of patients into a test group and a control group;
    identifying a plurality of patients in the test group at risk of non-adherence to medication;
    determining one or more actionable interventions for at-risk patients from the plurality of patients in the test group;
    aggregating data resulting from the one or more actionable interventions; and
    generating one or more dashboards for the medication adherence campaign based on the aggregated data.

11. A system comprising:
one or more processors; and
a memory, the memory storing instructions, which when executed cause the one or more processors to:
    receive a user-generated dataset, a clinical dataset, and a pharmacy dataset in association with a plurality of patients;
    train a machine learning model using a set of the user-generated dataset, the clinical dataset, and the pharmacy dataset of the plurality of patients, the set of the user-generated dataset, the clinical dataset, and the pharmacy dataset including known health risks of the plurality of patients to train the machine learning model, the machine learning model including a neural network model of assigning a weight to different patient health index scores;
    determine a social health index score of a patient from the plurality of patients based on user-generated data associated with the patient in the user-generated dataset;
    determine a clinical risk index score of the patient based on clinical data associated with the patient in the clinical dataset;
    determine a medication adherence index score of the patient based on pharmacy data associated with the patient in the pharmacy dataset;
    determine, using the machine learning model, a total health index score of the patient, the total health index score including a weighted combination of the social health index score, the clinical risk index score, and the medication adherence index score, the machine learning model assigning a weight to each of the social health index score, the clinical risk index score, and the medication adherence index score of the patient;
    determine an actionable intervention for managing a health risk in association with the patient based on one or more of the total health index score, the user-generated data, the clinical data, and the pharmacy data of the patient; and
    automatically initiate the actionable intervention.

12. The system of claim 11, wherein to determine the actionable intervention for managing the health risk in association with the patient, the instructions further cause the one or more processors to:
    determine, from an output of the machine learning model, that the health risk is a likelihood of the patient missing an upcoming healthcare appointment scheduled with a healthcare provider;
    identifying a communication channel preferred by the patient; and
    determining the actionable intervention to send an additional notification reminding the patient about the upcoming healthcare appointment through the identified communication channel.

13. The system of claim 11, wherein to determine the actionable intervention for managing the health risk in association with the patient, the instructions further cause the one or more processors to:
    determine, from an output of the machine learning model, that the health risk is a likelihood of a health condition progressing in the patient; and
    determine the actionable intervention to recommend content to the patient, the content associated with educating the patient about reducing a progression of the health condition.

14. The system of claim 11, wherein to determine the actionable intervention for managing the health risk in association with the patient, the instructions further cause the one or more processors to:
    determine, from an output of the machine learning model, that the health risk is a likelihood of a comorbidity in the patient; and
    determine the actionable intervention to schedule an appointment with a healthcare provider of the patient for medically testing a disease associated with the comorbidity in the patient.

15. The system of claim 11, wherein to determine the actionable intervention for managing the health risk in association with the patient, the instructions further cause the one or more processors to:
    determine, from an output of the machine learning model, that the health risk is a likelihood of a medication adherence score of the patient being less than a threshold by end of a predetermined time period; and
    determine the actionable intervention from a group of a digital intervention, an educational intervention, and a social intervention to facilitate the patient with adhering to taking their prescribed medication.

16. The system of claim 15, wherein the digital intervention includes sending a reminder notification through one or more of a phone call, text messaging, email, in-app messaging within a health care mobile application, and an interactive voice response.

17. The system of claim 15, wherein the educational intervention includes sending a comic strip including a story about a benefit associated with adhering to taking prescribed medication.

18. The system of claim 15, wherein the social intervention includes one or more of scheduling an appointment with a social work for a counseling session, informing a family member of the patient to help with medication adherence, and sending a reminder in a native language of the patient with limited English proficiency.

19. The system of claim 11, wherein the instructions further cause the one or more processors to:
    generate a dashboard for condition management, the dashboard providing access to one or more of protected health information indicators and status, educational content recommendations, medication planning and reminders, appointment management, and social and emotional support groups; and
    present the dashboard to the patient.

20. The system of claim 11, wherein the instructions further cause the one or more processors to:
    determine a population of patients to target for a medication adherence campaign;

divide the population of patients into a test group and a control group;
identify a plurality of patients in the test group at risk of non-adherence to medication;
determine one or more actionable interventions for at-risk patients from the plurality of patients in the test group;
aggregate data resulting from the one or more actionable interventions; and
generate one or more dashboards for the medication adherence campaign based on the aggregated data.

\* \* \* \* \*